(12) United States Patent
Huang et al.

(10) Patent No.: US 11,284,858 B1
(45) Date of Patent: Mar. 29, 2022

(54) SYSTEMS AND METHODS FOR PLANE-WAVE AND FAN-BEAM ULTRASOUND-WAVEFORM TOMOGRAPHY

(71) Applicant: TRIAD NATIONAL SECURITY, LLC, Los Alamos, NM (US)

(72) Inventors: Lianjie Huang, Los Alamos, NM (US); Kai Gao, Los Alamos, NM (US); Yunsong Huang, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 303 days.

(21) Appl. No.: 16/460,899

(22) Filed: Jul. 2, 2019

Related U.S. Application Data

(60) Provisional application No. 62/693,344, filed on Jul. 2, 2018.

(51) Int. Cl.
*G06K 9/00* (2006.01)
*A61B 8/13* (2006.01)
(Continued)

(52) U.S. Cl.
CPC .............. *A61B 8/13* (2013.01); *A61B 8/4483* (2013.01); *A61B 8/08* (2013.01); *G01N 29/0672* (2013.01); *G01N 2291/02466* (2013.01)

(58) Field of Classification Search
CPC ........... A61B 8/13; A61B 8/4483; A61B 8/08; G01N 2291/02466; G01N 29/0672
See application file for complete search history.

(56) References Cited

U.S. PATENT DOCUMENTS

| | | | | |
|---|---|---|---|---|
| 9,110,155 | B2* | 8/2015 | Nagae | ............... G01N 29/44 |
| 2009/0234230 | A1* | 9/2009 | Bercoff | ............... G10K 11/346 |
| | | | | 600/447 |

(Continued)

OTHER PUBLICATIONS

Zhang, Z., Huang, L., and Lin, Y., "Efficient implementation of ultrasound waveform tomography using source encoding," in [Ultrasonic Imaging, Tomography, and Therapy], Bosch, J. G. and Doyley, M. M., eds., Proc. SPIE 8320, doi: 10.1117/12.910969, 832003-1-10, SPIE, Bellingham, Washington (2012), 11 pages.

(Continued)

*Primary Examiner* — Solomon G Bezuayehu
(74) *Attorney, Agent, or Firm* — Lewis Roca Rothgerber Christie LLP

(57) ABSTRACT

A method for plane-wave or fan-beam ultrasound tomography includes: controlling, by a processor, a multi-channel ultrasound array controller to control a linear ultrasound transducer array to emit plane-wave or fan-beam ultrasound into a biological tissue, the linear ultrasound transducer array including a plurality of transducers; receiving, by the processor, plane-wave or fan-beam ultrasound waveform data from the transducers, the plane-wave or fan-beam ultrasound waveform data including reflections of the plane-wave or fan-beam ultrasound from the biological tissue; computing, by the processor, a synthetic ultrasound-waveform inversion from the received plane-wave or fan-beam ultrasound waveform data; and computing, by the processor, an image of the biological tissue from the synthetic ultrasound-waveform inversion.

16 Claims, 28 Drawing Sheets
(21 of 28 Drawing Sheet(s) Filed in Color)

(51) Int. Cl.
*A61B 8/00* (2006.01)
*A61B 8/08* (2006.01)
*G01N 29/06* (2006.01)

(56) References Cited

U.S. PATENT DOCUMENTS

| | | | | |
|---|---|---|---|---|
| 2013/0251222 | A1* | 9/2013 | Huang | A61B 8/5207 382/131 |
| 2014/0155746 | A1* | 6/2014 | Tanigawa | A61B 8/485 600/438 |
| 2014/0364737 | A1* | 12/2014 | Huang | G06T 5/001 600/447 |
| 2014/0371594 | A1* | 12/2014 | Flynn | G01S 15/8995 600/454 |
| 2015/0164467 | A1* | 6/2015 | Suetoshi | A61B 8/5207 600/408 |
| 2016/0209502 | A1* | 7/2016 | Kim | G01S 15/8915 |
| 2016/0310109 | A1* | 10/2016 | Park | A61B 8/5207 |
| 2020/0008779 | A1* | 1/2020 | Goksel | G01S 7/52049 |
| 2020/0037994 | A1* | 2/2020 | Song | G01S 15/8995 |

OTHER PUBLICATIONS

Lin, Y., Huang, L., and Zhang, Z., "Ultrasound waveform tomography with the totalvariation regularization for detection of small breast tumors," in [Ultrasonic Imaging, Tomography, and Therapy], Bosch, J. G. and Doyley, M. M., eds., Proc. SPIE 8320, doi: 10.1117/12.910765, 832002-1-9, SPIE, Bellingham, Washington (2012), 10 pages.

Lin, Y. and Huang, L., "Ultrasound waveform tomography with a modified total-variation regularization scheme," in [Ultrasonic Imaging, Tomography, and Therapy], Bosch, J. G. and Doyley, M. M., eds., Proc. SPIE 8675, doi: 10.1117/12.2007650, 86751F-1-9, SPIE, Bellingham, Washington (2013), 10 pages.

Zhang, Z. and Huang, L., "Ultrasound waveform tomography using wave-energy-based preconditioning," in [Ultrasonic Imaging, Tomography, and Therapy], Bosch, J. G. and Doyley, M. M., eds., Proc. SPIE 8675, doi: 10.1117/12.2007659, 86751G-1-10, SPIE, Bellingham, Washington (2013), 12 pages.

Zhang, Z. and Huang, L., "Efficient implementation of ultrasound waveform tomography using data blending," in [Ultrasonic Imaging and Tomography], Bosch, J. G. and Doyley, M. M., eds., Proc. SPIE 9040, 904010-1-9, SPIE, Bellingham, Washington (2014), 10 pages.

Huang, L., Lin, Y., Zhang, Z., Labyed, Y., Tan, S., Nguyen, N., Hansona, K., Sandoval, D., and Williamson, M., "Breast ultrasound waveform tomography: Using both transmission and reflection data, and numerical virtual point sources," in [Ultrasonic Imaging and Tomography], Bosch, J. G. and Doyley, M. M., eds., Proc. SPIE 9040, 90400T-1-12, SPIE, Bellingham, Washington (2014), 13 pages.

Lin, Y. and Huang, L., "Ultrasound waveform tomography with a spatially-variant regularization scheme," in [Ultrasonic Imaging and Tomography], Bosch, J. G. and Doyley, M. M., eds., Proc, SPIE 9040, 90401M-1-7, SPIE, Bellingham, Washington (2014), 8 pages.

Huang, L., Shin, J., Chen, T., Lin, Y., Intrator, M., Hanson, K., Epstein, K., Sandoval, D., and Williamson, M., "Breast ultrasound tomography with two parallel transducer arrays: preliminary clinical results," (2015), 11 pages.

Lin, Y. and Huang, L., "Ultrasound waveform tomography with the second-order total-generalized-variation regularization," in [Physics of Medical Imaging], Proc. SPIE 9783, SPIE, Bellingham, Washington (2016), 8 pages.

Huang, L., Shin, J., Chen, T., Lin, Y., Gao, K., Intrator, M., and Hanson, K., "Breast ultrasound tomography with two parallel transducer arrays," in [Physics of Medical Imaging], Proc. SPIE 9783, SPIE, Bellingham, Washington (2016), 13 pages.

* cited by examiner

SYSTEMS AND METHODS FOR PLANE-WAVE AND FAN-BEAM ULTRASOUND-WAVEFORM TOMOGRAPHY

CROSS-REFERENCE TO RELATED APPLICATION

This application claims the benefit of U.S. Provisional Patent Application No. 62/693,344 "SYSTEMS AND METHODS FOR PLANE-WAVE ULTRASOUND-WAVEFORM TOMOGRAPHY," filed in the United States Patent and Trademark Office on Jul. 2, 2018, the entire disclosure of which is incorporated by reference herein.

STATEMENT REGARDING FEDERALLY SPONSORED RESEARCH OR DEVELOPMENT

The United States government has rights in this invention pursuant to Contract No. 89233218CNA000001 between the United States Department of Energy/National Nuclear Security Administration and Triad National Security, LLC for the operation of Los Alamos National Laboratory.

FIELD

Aspects of embodiments of the present invention relate to the field of ultrasound tomography.

BACKGROUND

Ultrasound tomography is used in the medical field to reconstruct the mechanical properties of biological tissues (e.g., human body tissues) using ultrasound signals. For example, the reconstructed mechanical properties of tissues can be used for cancer characterization, such as characterizing tumors due to prostate cancer and breast cancer.

Early detection is important to reducing the death rate due to prostate-cancer. The prostate-specific antigen (PSA) blood test is the only technique widely used for prostate-cancer screening. However, the United States Preventive Services Task Force of the United States Department of Health and Human Services' Agency for Healthcare Research and Quality has recommended against PSA screening for prostate cancer because its benefits do not outweigh the resulting harms. The current "state-of-the-art" (but "crude") technique for detecting and characterizing prostate cancer involves combining PSA screening and random (systematic) biopsy, leading to overdiagnosis and/or underdiagnosis and overtreatment and/or undertreatment, respectively. PSA tests cannot distinguish aggressive and life-threatening from indolent and insignificant prostate cancers, and random biopsy can miss clinically significant (e.g., lethal) cancers, leading to under-diagnosis and under-treatment. Current PSA tests produce roughly 80% of false-positive results, leading to vast overdiagnosis and overtreatment and its associated harms.

SUMMARY

Aspects of embodiments of the present invention relate to systems and methods for applying plane-wave or fan-beam ultrasound-waveform inversion to reconstruct sound-speed, density, and attenuation values of tumors such as prostate tumors and breast tumors. In some embodiments of the present invention, an ultrasound-waveform inversion technique iteratively fits synthetic ultrasound waveforms with recorded ultrasound waveforms starting from an initial model. The technique is verified using synthetic ultrasound data for numerical prostate phantoms including of multiple tumors in homogeneous and heterogeneous background prostate tissues (generally, biological tissues). The reconstruction results demonstrate that plane-wave or fan-beam transrectal ultrasound-waveform tomography can accurately reconstruct the sound-speed values of prostate tumors for cancer characterization. Some embodiments of the present invention relate to an implementation of a transrectal ultrasound tomography system using a 256-channel Verasonics® Vantage system and a GE® intracavitary curved linear array to acquire plane-wave or fan-beam ultrasound reflection data for transrectal ultrasound tomography.

According to one embodiment of the present invention, a system for plane-wave and fan-beam ultrasound tomography includes: a linear ultrasound transducer array including a plurality of transducers; a multi-channel ultrasound array controller configured to control the linear ultrasound transducer array; a host controller including a processor and memory, the memory storing instructions that, when executed by the processor, cause the processor to: control the multi-channel ultrasound array controller to control the linear ultrasound transducer array to emit plane-wave or fan-beam ultrasound into a biological tissue; receive plane-wave or fan-beam ultrasound waveform data from the transducers, the plane-wave or fan-beam ultrasound waveform data including reflections of the plane-wave or fan-beam ultrasound from the biological tissue; compute a synthetic ultrasound-waveform inversion from the received plane-wave or fan-beam ultrasound waveform data; and compute an image of the biological tissue from the synthetic ultrasound-waveform inversion.

The memory may further store instructions that, when executed by the processor of the host controller, cause the host controller to compute the ultrasound waveform inversion by iteratively minimizing a plane-wave or fan-beam misfit function:

$$\chi(m) = \sum_{t,s,r} \frac{1}{2} \|d - f(m)\|_2^2,$$

where d is the plane-wave or fan-beam ultrasound waveform data and f(m) is an iteration of a synthetic ultrasound-waveform inversion, m is a physical parameter model, and a data misfit is accumulated for all recording time (t) of the waveform, all the transducers (s) and all the receivers (r), and where the computed synthetic ultrasound-waveform inversion corresponds to the iteration of the synthetic ultrasound-waveform inversion that minimizes $\chi(m)$.

The physical parameter model m may include sound speed values, density values, and attenuation values.

The memory may further store instructions that, when executed by the processor of the host controller, cause the host controller to compute the ultrasound waveform inversion by iteratively minimizing a plane-wave or fan-beam misfit function:

$$\chi(m) = \sum_{t,s,r} \frac{1}{2} \left\| \sum_i^{s'} d_i(\Delta t_i, p_j) - \sum_i^{s'} f_i(m, \Delta t_i, p_j) \right\|_2^2$$

where s' is the number of plane-wave or fan-beam gathers, $d_i$ and $f_i$ are an i-th single-point received ultrasound waveform data and an i-th synthetic ultrasound-waveform inversion data gather of, respectively, a plurality of gathers of received ultrasound data and a plurality of gathers of synthetic ultrasound-waveform inversion data, and $\Delta t_i$ represents the time delay corresponding to the i-th single-point gather, and $p_j$ represents a ray parameter of a j-th plane-wave or fan-beam data gather with $1 \leq j \leq s'$, where the computed synthetic ultrasound-waveform inversion corresponds to the iteration of the synthetic ultrasound-waveform inversion that minimizes $\chi(m)$.

The function $\chi(m)$ may further include a regularization term $\mathcal{R}(m)$ added to the plane-wave or fan-beam misfit function, and the regularization term may be:

$$\mathcal{R}(m) = \mathrm{argmin}_m + \lambda_1 \|\nabla m - w\|_l^l + \lambda_2 \|\varepsilon(w)\|_l^l$$

where w is an auxiliary variable, the norm $l=\frac{1}{2}$, $\nabla$ is the gradient operator and $\varepsilon$ is the symmetric gradient operator in the second-order form.

The memory may further store instructions that, when executed by the processor of the host controller, cause the host controller to compute the ultrasound waveform inversion by iteratively minimizing a plane-wave or fan-beam misfit function using an alternating direction minimization strategy and a split-Bregman iteration technique.

The memory may further store instructions that, when executed by the processor of the host controller, cause the host controller to compute the ultrasound waveform inversion by iteratively minimizing a plane-wave or fan-beam misfit function $\chi$ using an adjoint-state method to compute a gradient for the plane-wave or fan-beam misfit function, and wherein the gradient is computed by a zero-lag time cross-correlation between a source forward-propagated wavefield and a back-propagated adjoint-source wavefield:

$$\nabla \chi = - \sum_{t,s',r} \frac{\partial^2 p}{\partial t^2} p^\dagger$$

where p is the source wavefield and $p^\dagger$ is the adjoint-source wavefield.

A nonlinear conjugate-gradient inversion framework may be used to update the physical property model m after computing a gradient in each iteration, where a k-th model $m^k$ is updated to compute a k+1-th model $m^{k+1}$ in accordance with:

$$m^{k+1} \leftarrow m^k + \alpha g^k$$

where $\alpha$ is a step length computed using a model perturbation approach, and $g^k$ is the search direction in the k-th iteration computed for a $g^{k+1}$ search direction for a k+1-th iteration using the Polak-Ribière formula:

$$g^{k+1} \leftarrow -(\nabla \chi)^{k+1} + \max\left\{ \frac{[(\nabla \chi)^{k+1}]^T [(\nabla \chi)^{k+1} - (\nabla \chi)^k]}{[(\nabla \chi)^k]^T (\nabla \chi)^k} \right\} g^k,$$

where $(\nabla \chi)^k$ is the gradient in the k-th iteration, and where T represents a transpose operation.

The memory may further store instructions that, when executed by the processor of the host controller, cause the host controller to: control the linear ultrasound transducer array to emit plane-wave or fan-beam ultrasound into the biological tissue at a plurality of different angles; receive plane-wave or fan-beam ultrasound data including reflections of the plane-wave or fan-beam ultrasound at each of the plurality of different angles; and compute a plurality of separate synthetic ultrasound-waveform inversions, each corresponding to the plane-wave or fan-beam ultrasound data received from plane-wave or fan-beam ultrasound emitted at one of the different angles, and wherein the image of the biological tissue is computed from the separate synthetic ultrasound-waveform inversions of each of the different angles.

According to one embodiment of the present invention, a method for plane-wave or fan-beam ultrasound tomography includes: controlling, by a processor, a multi-channel ultrasound array controller to control a linear ultrasound transducer array to emit plane-wave or fan-beam ultrasound into a biological tissue, the linear ultrasound transducer array including a plurality of transducers; receiving, by the processor, plane-wave or fan-beam ultrasound waveform data from the transducers, the plane-wave or fan-beam ultrasound waveform data including reflections of the plane-wave or fan-beam ultrasound from the biological tissue; computing, by the processor, a synthetic ultrasound-waveform inversion from the received plane-wave or fan-beam ultrasound waveform data; and computing, by the processor, an image of the biological tissue from the synthetic ultrasound-waveform inversion.

The method may further include computing the ultrasound waveform inversion by iteratively minimizing a plane-wave or fan-beam misfit function:

$$\chi(m) = \sum_{t,s,r} \frac{1}{2} \|d - f(m)\|_2^2,$$

where d is the plane-wave or fan-beam ultrasound waveform data and f(m) is an iteration of a synthetic ultrasound-waveform inversion, m is a physical parameter model, and a data misfit is accumulated for all recording time (t) of the waveform, all the transducers (s) and all the receivers (r), and where the computed synthetic ultrasound-waveform inversion corresponds to the iteration of the synthetic ultrasound-waveform inversion that minimizes $\chi(m)$.

The physical parameter model m may include sound speed values, density values, and attenuation values.

The method may further include computing the ultrasound waveform inversion by iteratively minimizing a plane-wave or fan-beam misfit function:

$$\chi(m) = \sum_{t,s',r} \frac{1}{2} \left\| \sum_i^s d_i(\Delta t_i, p_j) - \sum_i^s f_i(m, \Delta t_i, p_j) \right\|_2^2$$

where s' is the number of plane-wave or fan-beam gathers, $d_i$ and $f_i$ are an i-th single-point received ultrasound waveform data and an i-th synthetic ultrasound-waveform inversion data gather of, respectively, a plurality of gathers of received ultrasound data and a plurality of gathers of synthetic ultrasound-waveform inversion data, and $\Delta t_i$ represents the time delay corresponding to the i-th single-point gather, and $p_j$ represents a ray parameter of a j-th plane-wave or fan-beam data gather with $1 \leq j \leq s'$, where the computed synthetic ultrasound-waveform inversion corresponds to the iteration of the synthetic ultrasound-waveform inversion that minimizes $\chi(m)$.

The function $\chi(m)$ may further include a regularization term $\mathcal{R}(m)$ added to the plane-wave or fan-beam misfit function, and the regularization term may be:

$$\mathcal{R}(m) = \mathrm{argmin}_m + \lambda_1 \|\nabla m - w\|_l^l + \lambda_2 \|\varepsilon(w)\|_l^l$$

where w is an auxiliary variable, the norm l=½, ∇ is the gradient operator and ε is the symmetric gradient operator in the second-order form.

The method may further include computing the ultrasound waveform inversion by iteratively minimizing a plane-wave or fan-beam misfit function using an alternating direction minimization strategy and a split-Bregman iteration technique.

The method may further include computing the ultrasound waveform inversion by iteratively minimizing a plane-wave or fan-beam misfit function χ using an adjoint-state method to compute a gradient for the plane-wave or fan-beam misfit function, and the gradient may be computed by a zero-lag time cross-correlation between a source forward-propagated wavefield and a back-propagated adjoint-source wavefield:

$$\nabla \chi = -\sum_{t,s',r} \frac{\partial^2 p}{\partial t^2} p^\dagger$$

where p is the source wavefield and $p^\dagger$ is the adjoint-source wavefield.

A nonlinear conjugate-gradient inversion framework may be used to update the physical property model m after computing a gradient in each iteration, where a k-th model $m^k$ is updated to compute a k+1-th model $m^{k+1}$ in accordance with:

$$m^{k+1} \leftarrow m^k + \alpha g^k$$

where α is a step length computed using a model perturbation approach, and $g^k$ is the search direction in the k-th iteration computed for a $g^{k+1}$ search direction for a k+1-th iteration using the Polak-Ribière formula:

$$g^{k+1} \leftarrow -(\nabla \chi)^{k+1} + \max\left\{\frac{[(\nabla \chi)^{k+1}]^T[(\nabla \chi)^{k+1} - (\nabla \chi)^k]}{[(\nabla \chi)^k]^T(\nabla \chi)^k}\right\}g^k,$$

where $(\nabla \chi)^k$ is the gradient in the k-th iteration, and where T represents a transpose operation.

The method may further include: controlling the linear ultrasound transducer array to emit plane-wave or fan-beam ultrasound into the biological tissue at a plurality of different angles; receiving plane-wave or fan-beam ultrasound data including reflections of the plane-wave or fan-beam ultrasound at each of the plurality of different angles; and computing a plurality of separate synthetic ultrasound-waveform inversions, each corresponding to the plane-wave or fan-beam ultrasound data received from plane-wave or fan-beam ultrasound emitted at one of the different angles, wherein the image of the biological tissue is computed from the separate synthetic ultrasound-waveform inversions of each of the different angles.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate exemplary embodiments of the present invention, and, together with the description, serve to explain the principles of the present invention.

DETAILED DESCRIPTION

In the following detailed description, only certain exemplary embodiments of the present invention are shown and described, by way of illustration. As those skilled in the art would recognize, the invention may be embodied in many different forms and should not be construed as being limited to the embodiments set forth herein.

As noted above, medical imaging techniques are used to characterize tumors. However, comparative imaging techniques do not reliably characterize prostate cancers. One comparative technique is transrectal ultrasound (TRUS) imaging, which is a "qualitative" technique, and which has only very limited capability for localizing and staging of prostate cancer. TRUS is generally used merely for biopsy needle guidance and the prostate size measurement. Elastography is another comparative technique that was developed to overcome the limitations of TRUS, but clinical studies show that elastography should not be used as a routine tool for prostate cancer detection because of its limited accuracy in characterizing tumors. X-ray Computed Tomography (CT) has only a limited role in imaging prostate cancer because of its poor soft-tissue contrast resolution, which does not allow precise distinction between the internal and external anatomy of the prostate. Magnetic Resonance Imaging (MRI) is a promising technique, but is expensive and not portable.

Plane-wave ultrasound imaging is a recently-developed imaging modality that has the capacity to increase image quality and imaging depth. However, analysis algorithms are needed to reconstruct images from the waveforms that are captured using plane-wave ultrasound imaging.

Aspects of embodiments of the present invention relate to a plane-wave or fan-beam ultrasound-waveform inversion algorithm for sound-speed reconstruction of tissues such as the prostate and breast. At least some aspects of embodiments of the present invention apply full-waveform inversion of plane-wave or fan-beam ultrasound reflection data instead of synthetic aperture ultrasound data. This change can improve the signal-to-noise ratios, thereby also improving inversion results. The data acquisition time for plane wave ultrasound can be much faster than that for synthetic aperture ultrasound. Aspects of embodiments of the present invention also relate to the use of a high-order regularization term to enhance the inversion accuracy and accelerate the inversion convergence.

In addition, some aspects of embodiments of the present invention relate to a transrectal ultrasound tomography system using a 256-channel Verasonics® Vantage system and a GE® intracavitary curved linear array to acquire plane-wave or fan-beam ultrasound reflection data for ultrasound tomography. Experimental results demonstrate that plane-wave or fan-beam ultrasound-waveform inversion can accurately reconstruct the sound-speed values of prostate tumors for cancer characterization.

Figures 1A, 1B:
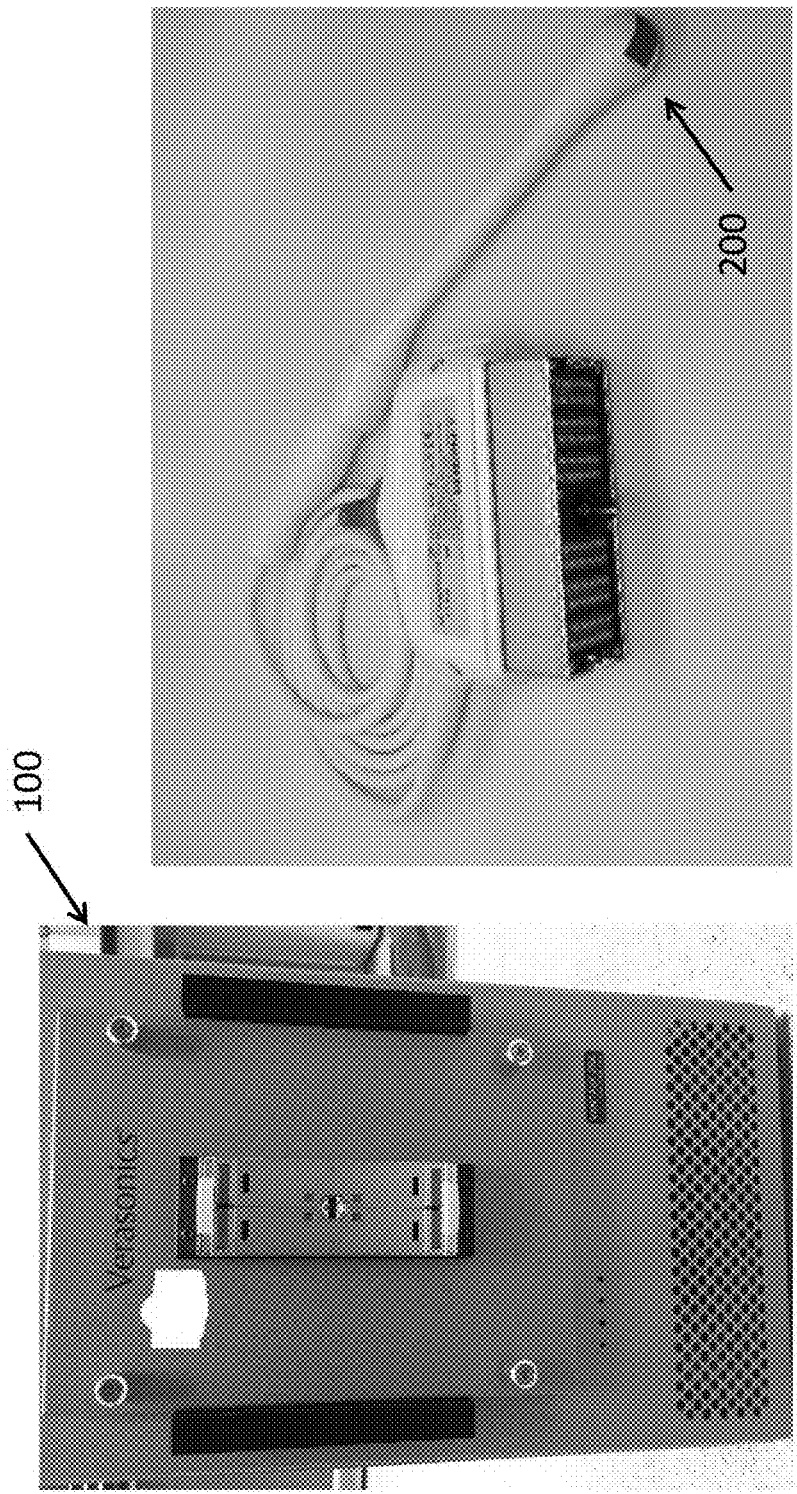
FIG. 1(a) depicts a Verasonics® Vantage 256 system used in a plane-wave or fan-beam ultrasound system according to one embodiment of the present invention.
FIG. 1(b) depicts a GE® intracavitary curved linear array used in a plane-wave or fan-beam ultrasound system according to one embodiment of the present invention.

FIG. 1(a) depicts a Verasonics® Vantage 256 system used in a plane-wave or fan-beam ultrasound system according to one embodiment of the present invention. The Verasonics® Vantage data acquisition system includes an adapter and a host controller 100 that is equipped with and can be controlled by a software package in MathWorks® MATLAB®. This system allows for data acquisition up to 100,000 frames/second and enables highly parallelized software beamforming.

FIG. 1(b) depicts a GE® (General Electric) intracavitary curved linear array 200 used in a plane-wave or fan-beam ultrasound system according to one embodiment of the present invention. The center frequency of the GE curved linear transducer array is 5.8 MHz with a bandwidth of 75%. The radius of curvature of the curved linear transducer array is 10.1 mm. This transducer array is compatible with the Verasonics Vantage 256 system and, in some embodiments of the present invention, is used in conjunction with the system.

While aspects of embodiments of the present invention will be discussed in the context of a Verasonics® Vantage data acquisition system and a GE® intracavitary curved linear array, embodiments of the present invention are not limited thereto and can also be applied using different data acquisition systems and different intracavity linear ultrasound arrays.

Figure 1C:
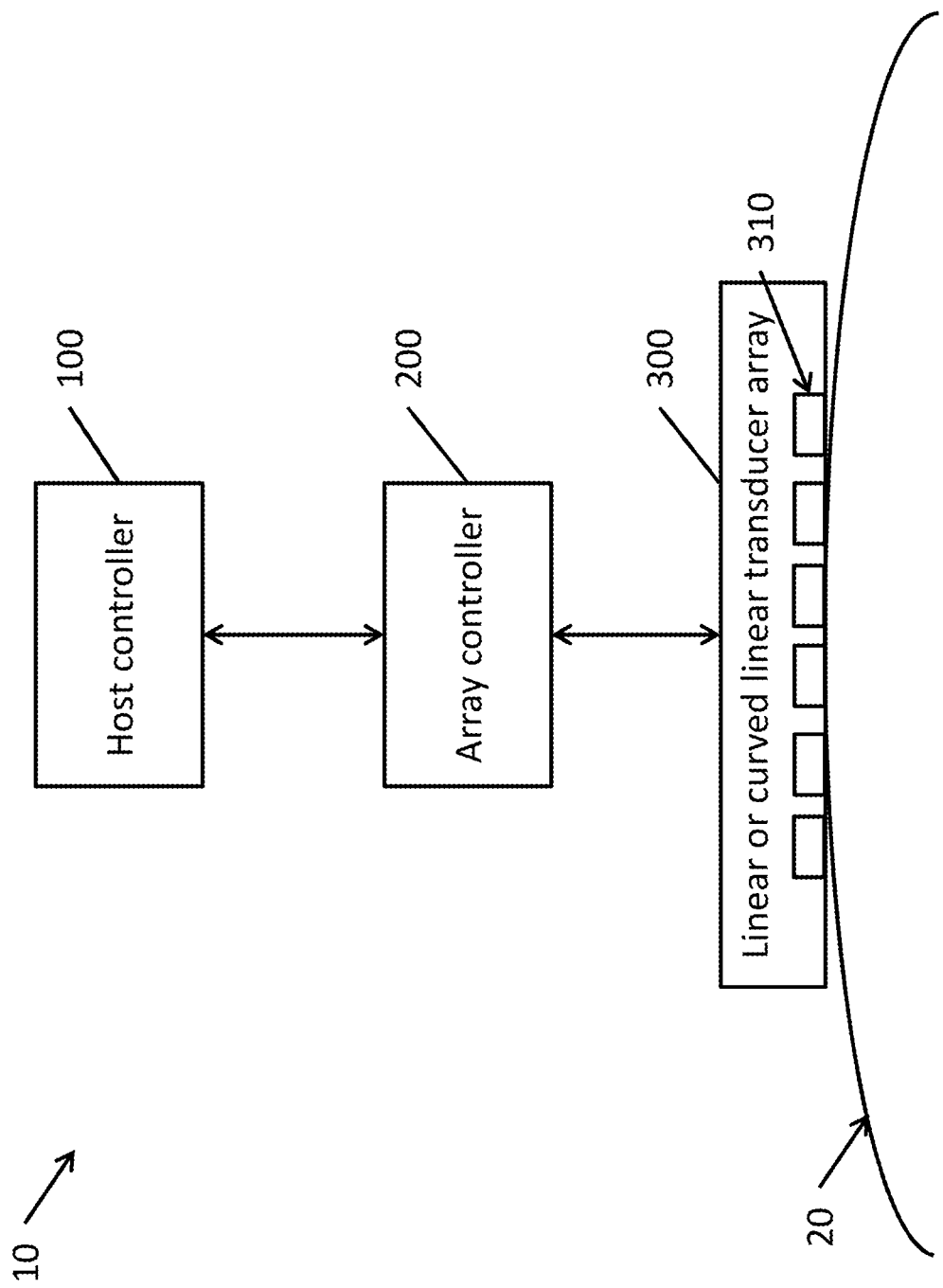
FIG. 1(c) is a schematic block diagram of an ultrasound scanning system according to one embodiment of the present invention.

FIG. 1(c) is a schematic block diagram of an ultrasound scanning system according to one embodiment of the present invention. As shown in FIG. 1(c), the ultrasound scanning system 10 may be configured to image biological tissue 20 (e.g., of a person). The ultrasound scanning system 10 includes a host controller. The host controller may include, for example, a processor, memory, and a peripheral bus, where the memory stores computer instructions for controlling the processor, and data, and the processor may be controlled, by the instructions, to control peripheral devices using the peripheral bus and to receive data from the peripheral bas and to store the received data in the memory. The system may also include a transducer array controller 200 (or array controller) configured to receive commands (e.g., from the host controller 100) and to control a linear transducer array 300 based on the commands (e.g., to transmit analog or digital signals to the linear transducer array to control transducers 310 to transmit ultrasound waveforms into the biological tissue 20 or to convert signals (e.g., analog signals) representing signals detected by the linear transducer array and convert the received signals into digital data to be stored in the memory of the host controller 100. The linear transducer array 300 may include a plurality of ultrasound transducers 310 (e.g., transmitters, receivers, transceivers, or combinations thereof), arranged in an array (e.g., a linear array).

Figure 1D:
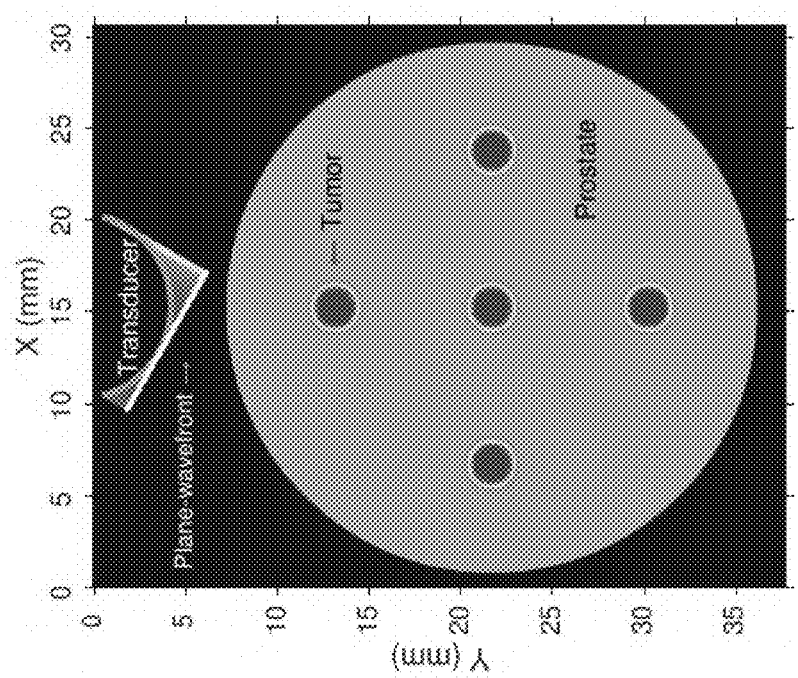
FIGS. 1(d), 1(e), and 1(f) are schematic illustrations of transrectal ultrasound with plane-wave or fan-beam scanning at different incident angles.
Figure 1E:
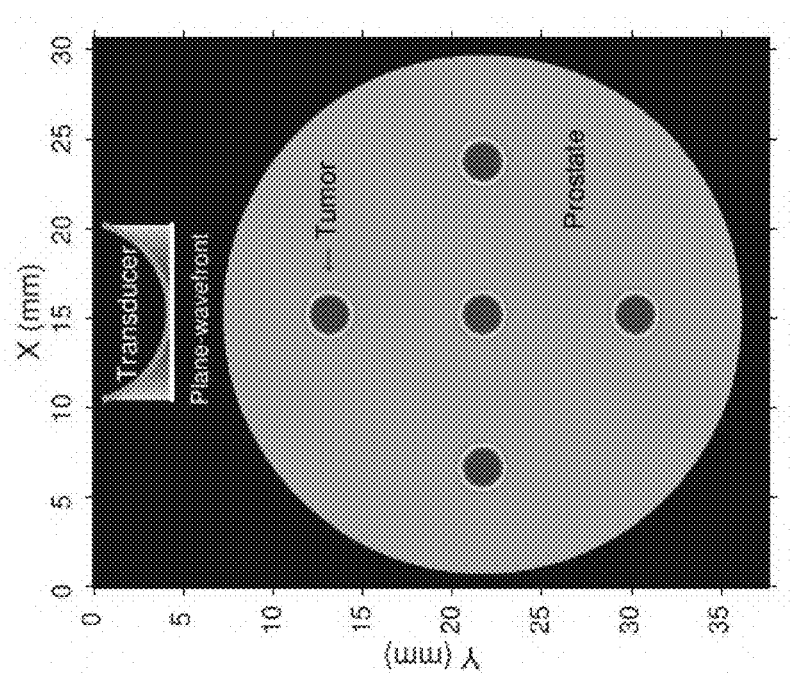
Figure 1F:
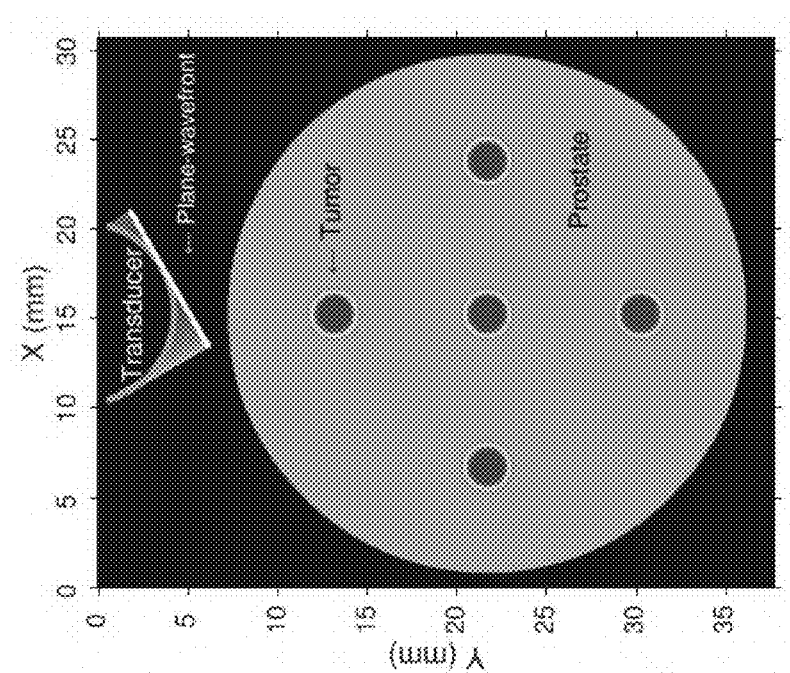

FIGS. 1(d), 1(e), and 1(f) are schematic illustrations of transrectal ultrasound with plane-wave scanning at different incident angles. As shown in FIGS. 1(d), 1(e), and 1(f), the Verasonics® Vantage data acquisition system enables the firing of plane waves from the intracavity linear ultrasound array (e.g., a transrectal ultrasound transducer array) and the illumination of the prostate along different incident angles. Plane-wave or fan-beam ultrasound can achieve a higher signal-to-noise ratio and record ultrasound reflection data from deeper target imaging regions compared to synthetic aperture ultrasound, leading to improved image quality.

Ultrasound-waveform inversion, or full-waveform inversion of ultrasound data, inverts ultrasound waveform data for sound-speed values and other mechanical properties of tissues and tumors, such as the density and attenuation. Ultrasound-waveform inversion is an iterative approach, starting from an initial model and minimizing the data misfit between synthetic and recorded ultrasound waveforms. The iteration process stops when the data misfit does not decrease anymore. Some ultrasound-waveform inversion techniques, in accordance with embodiments of the present invention, take a multi-scale inversion approach and apply a regularization scheme to improve the inversion robustness and inversion convergence rate.

For comparative synthetic-aperture ultrasound data, ultrasound-waveform inversion needs to be performed for each waveform emitted from each transducer element in the transducer array. Therefore, the number of ultrasound-waveform inversion processes is the same of the number of ultrasound transducer elements. Generally, the number of ultrasound transducer elements (generally in the range of hundreds to thousands) is much higher than the number of ultrasound plane-wave or fan-beams (generally in the range of twenty to thirty) in accordance with embodiments of the present invention. Therefore, the data volume of plane-wave or fan-beam ultrasound is much smaller than that of synthetic-aperture ultrasound. In addition, embodiments of the present invention allow the use of a smaller number of ultrasound-waveform inversion processes and therefore the computational efficiency of plane-wave or fan-beam ultrasound-waveform inversion can be significantly better (e.g., higher efficiency) than that for the comparative synthetic-aperture ultrasound technique, as discussed in more detail below.

Aspects of embodiments of the present invention relate to applying ultrasound-waveform inversion algorithms to reconstruct sound-speed values of prostate tumors using plane-wave or fan-beam ultrasound reflection data. Some aspects of embodiments of the present invention relate to the use of a finite-difference method to solve the acoustic wave equation in heterogeneous media for the forward and inverse modelings in ultrasound-waveform inversion. For the sake of convenience, the below numerical examples use the same configuration of 192 transducer elements with a center frequency of 5.8 MHz, but embodiments of the present invention are not limited thereto.

Examples of ultrasound waveform inversion algorithms that are applied to the plane-wave ultrasound reflection data are described in, for example:

Zhang, Z., Huang, L., and Lin, Y., "Efficient implementation of ultrasound waveform tomography using source encoding," in [Ultrasonic Imaging, Tomography, and Therapy], Bosch, J. G. and Doyley, M. M., eds., Proc. SPIE 8320, doi: 10.1117/12.910969, 832003-1-10, SPIE, Bellingham, Wash. (2012).

Lin, Y., Huang, L., and Zhang, Z., "Ultrasound waveform tomography with the total-variation regularization for detection of small breast tumors," in [Ultrasonic Imaging, Tomography, and Therapy], Bosch, J. G. and Doyley, M. M., eds., Proc. SPIE 8320, doi: 10.1117/12.910765, 832002-1-9, SPIE, Bellingham, Wash. (2012).

Lin, Y. and Huang, L., "Ultrasound waveform tomography with a modified total-variation regularization scheme," in [Ultrasonic Imaging, Tomography, and Therapy], Bosch, J. G. and Doyley, M. M., eds., Proc. SPIE 8675, doi: 10.1117/12.2007650, 86751F-1-9, SPIE, Bellingham, Wash. (2013).

Zhang, Z. and Huang, L., "Ultrasound waveform tomography using wave-energy-based preconditioning," in [Ultrasonic Imaging, Tomography, and Therapy], Bosch, J. G. and Doyley, M. M., eds., Proc. SPIE 8675, doi: 10.1117/12.2007659, 86751G-1-10, SPIE, Bellingham, Wash. (2013).

Zhang, Z. and Huang, L., "Efficient implementation of ultrasound waveform tomography using data blending," in [Ultrasonic Imaging and Tomography], Bosch, J. G. and Doyley, M. M., eds., Proc. SPIE 9040, 904010-1-9, SPIE, Bellingham, Wash. (2014).

Huang, L., Lin, Y., Zhang, Z., Labyed, Y., Tan, S., Nguyen, N., Hansona, K., Sandoval, D., and Williamson, M., "Breast ultrasound waveform tomography: Using both transmission and reflection data, and numerical virtual point sources," in [Ultrasonic Imaging and Tomography], Bosch, J. G. and Doyley, M. M., eds., Proc. SPIE 9040, 90400T-1-12, SPIE, Bellingham, Wash. (2014).

Lin, Y. and Huang, L., "Ultrasound waveform tomography with a spatially-variant regularization scheme," in [Ultrasonic Imaging and Tomography], Bosch, J. G. and Doyley, M. M., eds., Proc. SPIE 9040, 90401M-1-7, SPIE, Bellingham, Wash. (2014).

Huang, L., Shin, J., Chen, T., Lin, Y., Intrator, M., Hanson, K., Epstein, K., Sandoval, D., and Williamson, M., "Breast ultrasound tomography with two parallel transducer arrays: preliminary clinical results," (2015).

Lin, Y. and Huang, L., "Ultrasound waveform tomography with the second-order total-generalized-variation regularization," in [Physics of Medical Imaging], Proc. SPIE 9783, SPIE, Bellingham, Wash. (2016).

Huang, L., Shin, J., Chen, T., Lin, Y., Gao, K., Intrator, M., and Hanson, K., "Breast ultrasound tomography with two parallel transducer arrays," in [Physics of Medical Imaging], Proc. SPIE 9783, SPIE, Bellingham, Wash. (2016).

Figure 2A:
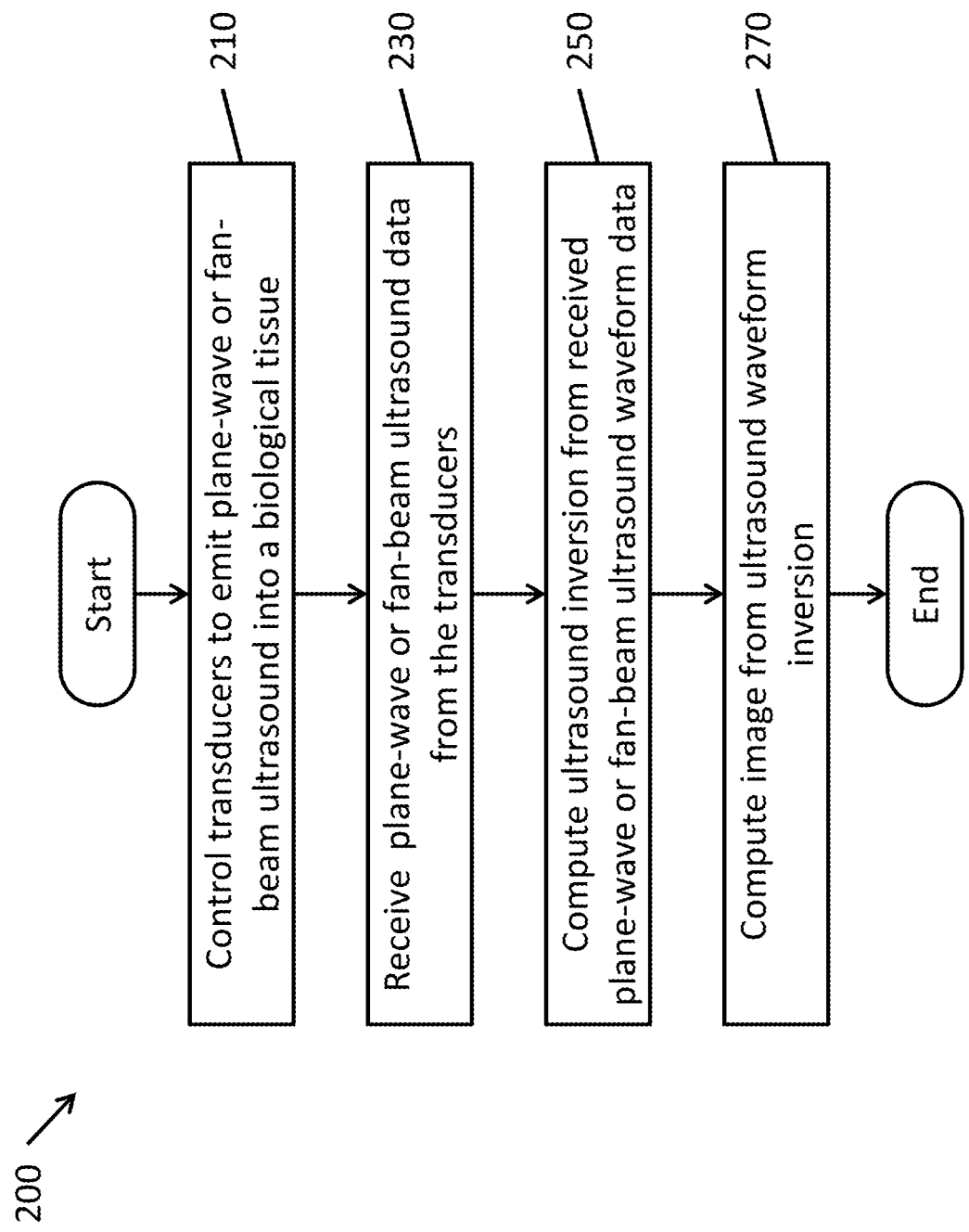
FIG. 2(a) is a flowchart of a method of imaging a biological tissue using a plane-wave or fan-beam ultrasound according to one embodiment of the present invention.

FIG. 2(a) is a flowchart of a method 200 of imaging a biological tissue using a plane-wave ultrasound according to one embodiment of the present invention. Referring to FIG. 2(a), in operation 210, the host controller 100 controls the transducers of the linear array 300, via the array controller 200, to emit plane-wave or fan-beam ultrasound into a biological tissue 20 (e.g., a prostate). In operation 230, the host controller 100 receives plane-wave or fan-beam ultrasound data from the transducers. As noted above, the transducers 310 of the linear array 300 may generate an analog electrical signal, which may be processed by the array controller 200 (e.g., using an analog to digital converter) to produce digital ultrasound data that is transmitted to the host controller 100. In operation 250, an ultrasound inversion is computed from the received plane-wave or fan-beam ultrasound data, as described in more detail below. In operation 270, the inverted ultrasound waveform data is used to generate an image (e.g., a bitmap) for analysis (e.g., displaying the generated image to a medical professional such as a doctor).

Figure 2B:
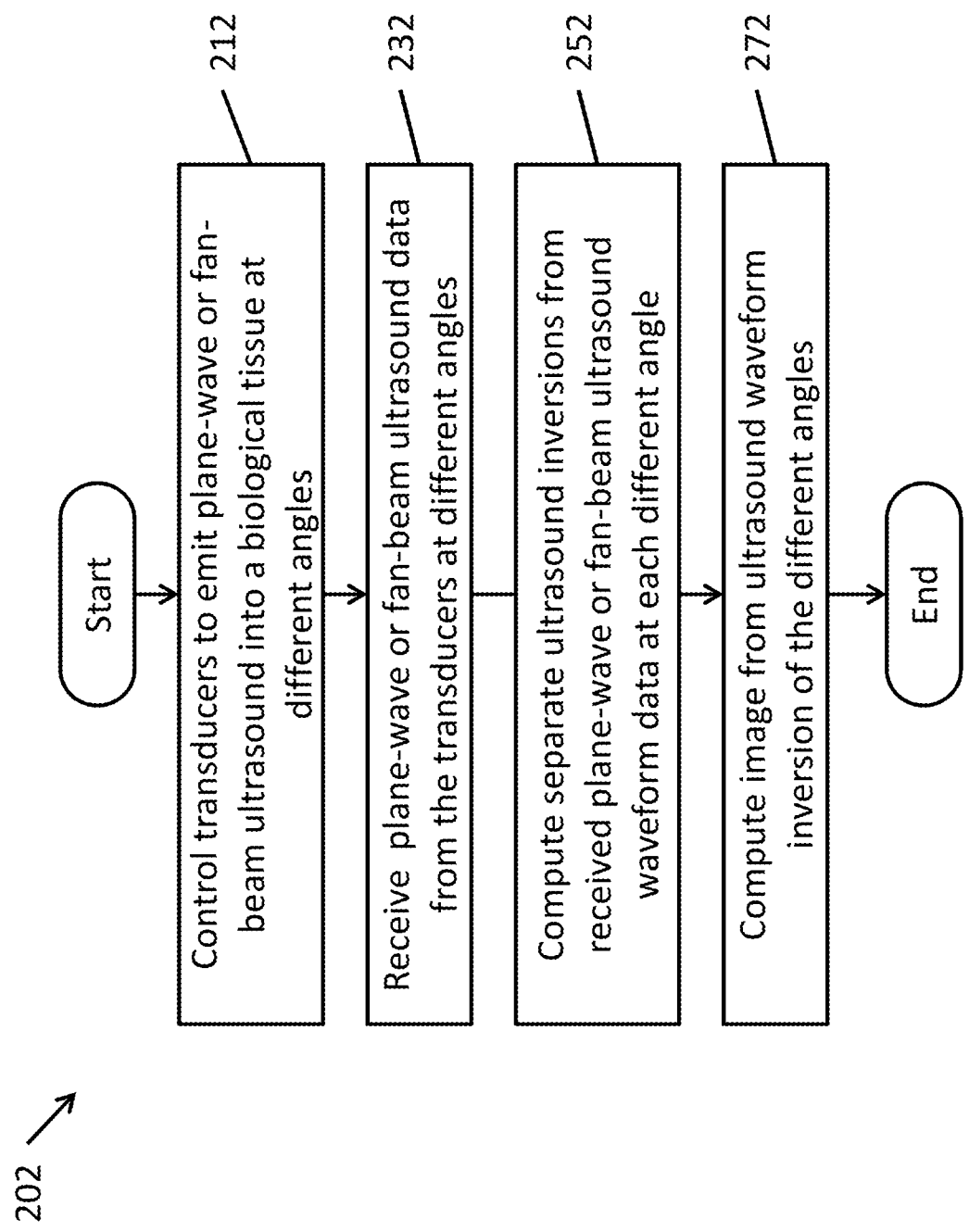
FIG. 2(b) is a flowchart of a method of imaging a biological tissue using a plane-wave or fan-beam ultrasound according to one embodiment of the present invention.

FIG. 2(b) is a flowchart of a method 202 of imaging a biological tissue using a plane-wave ultrasound from multiple different angles according to one embodiment of the present invention. The method 202 shown in FIG. 2(b) is similar to the method 200 shown in FIG. 2(a), and further relates to capturing ultrasound data from multiple angles. In operation 212, the host controller 100 controls the transducers of the linear array 300, via the array controller 200, to emit plane-wave ultrasound into a biological tissue 20 (e.g., a prostate) at multiple different angles. This may relate to, for example, transmitting plane-wave ultrasound in one position with respect to the biological tissue 20, repositioning the linear transducer array 300, and transmitting plane-wave ultrasound from the new position, and repeating as necessary or desired from different angles. In operation 230, the host controller 100 receives the plane-wave ultrasound data captured from multiple different angles. In operation 250, an ultrasound inversion is computed from the received plane-wave ultrasound data for each of the different angles (e.g., the data for each angle is independently inverted), as described in more detail below. In operation 270, the inverted ultrasound waveform data is combined and used to generate an image for analysis.

As noted above, a plane-wave or fan-beam data inversion algorithm is used (e.g., in operation 250 or 252, above) to invert the received plane-wave or fan-beam data, which is then used to synthesize an image. In a plane-wave or fan-beam ultrasound-waveform tomography algorithm according to one embodiment of the present invention, the goal of the inversion algorithm is to minimize the difference between the observed ultrasound waveform signals and the numerical synthetic ultrasound waveform signals according to the function $$\chi(m) = \sum_{t,s,r} \frac{1}{2} \|d - f(m)\|_2^2,$$

where d is the observed data (e.g., the received plane-wave or fan-beam ultrasound waveform data) and f(m) is the synthetic data (e.g., synthesized ultrasound-waveform inversion), m is the physical parameter model such as the sound speed, density, and attenuation, and t, s, r indicates that the data misfit is accumulated for all the recording time (t), all the transducers (s) and all the receivers (r). The resulting computed synthetic ultrasound-waveform inversion corresponds to the iteration of the synthetic ultrasound-waveform inversion that minimizes $\chi(m)$. In the case where there are multiple sets of data to invert, such as in operation 252 above, the technique is performed independently on each set of data (e.g., either in parallel or serially). In particular, some embodiments of the present invention relate to an iterative technique in which the numerical synthetic ultrasound waveform signal f(m) is updated during each iteration to reduce the difference $\chi(m)$, in accordance with a numerically computed gradient until the computed synthetic data f(m) converges to a solution with a minimal distance $\chi(m)$.

This inversion problem is a highly nonlinear, ill-posed minimization problem. To accelerate the convergence for complex models, aspects of embodiments of the present invention use a modified misfit function using plane-wave or fan-beam data gathers to enhance the signal-to-noise ratio of the observed data and reduce the computational costs:

$$\chi(m) = \sum_{t,s',r} \frac{1}{2} \left\| \sum_i^s d_i(\Delta t_i, p_j) - \sum_i^s f_i(m, \Delta t_i, p_j) \right\|_2^2,$$

where s' is the number of plane-wave or fan-beam gathers, $d_i$ and $f_i$ are the i-th single-point observed data gather and synthetic data gather, respectively, and $\Delta t_i$ represents the time delay corresponding to the i-th single-point gather, and $p_j$ represents the ray parameter of the j-th plane-wave or fan-beam data gather with $1 \leq j \leq s'$. The resulting computed synthetic ultrasound-waveform inversion corresponds to the iteration of the synthetic ultrasound-waveform inversion that minimizes $\chi(m)$. A series of $p_j$ with both negative and positive values is chosen to provide good coverage of the region of interest, such as the prostate tumors and the breast tumors.

In addition, in some embodiments, a regularization term $\mathcal{R}(m)$ is added to the plane-wave or fan-beam misfit function to accelerate the convergence:

$$\chi(m) = \sum_{t,s',r} \frac{1}{2} \left\| \sum_i^s d_i(\Delta t_i, p_j) - \sum_i^s f_i(m, \Delta t_i, p_j) \right\|_2^2 + \mathcal{R}(m),$$

where the high-order regularization term itself is defined through a minimization problem:

$$\mathcal{R}(m) = \operatorname{argmin}_m + \lambda_1 \|\nabla m - w\|_l^l + \lambda_2 \|\varepsilon(w)\|_l^l$$

where w is an auxiliary variable, the norm $l=\frac{1}{2}$, $\nabla$ is the gradient operator and $\varepsilon$ is the symmetric gradient operator in the second-order form. In some embodiments, the above minimization problem is solved using an alternating direction minimization strategy and split-Bregman iteration technique.

In some embodiments of the present invention, the adjoint-state method is used to compute the gradient for the misfit function, where we obtain the gradient by the zero-lag time cross-correlation between the source forward-propagated source wavefield and back-propagated adjoint-source wavefield:

$$\nabla \chi = -\sum_{t,s',r} \frac{\partial^2 p}{\partial t^2} p^\dagger,$$

where p is the source wavefield and $p^\dagger$ is the adjoint-source wavefield.

In some embodiments, the nonlinear conjugate-gradient inversion framework is used to update the physical property model m after computing the gradient in each iteration. For instance, the model update in the k+1-th iteration is:

$$m^{k+1} \leftarrow m^k + \alpha g^k$$

where $\alpha$ is the optimal step length computed using a model perturbation approach, $g^k$ is the search direction in the k-th iteration computed using the Polak-Ribière formula:

$$g^{k+1} \leftarrow -(\nabla \chi)^{k+1} + \max\left\{ \frac{[(\nabla \chi)^{k+1}]^T [(\nabla \chi)^{k+1} - (\nabla \chi)^k]}{[(\nabla \chi)^k]^T (\nabla \chi)^k} \right\} g^k,$$

with $(\nabla \chi)^k$ being the gradient in the k-th iteration, and with T representing transpose.

The iterative inversion algorithm terminates when the data residual is adequately small and reaches a threshold (e.g., a pre-defined threshold).

Numerical analysis was performed to compare the capability of plane-wave or fan-beam ultrasound-waveform inversion to reconstruct sound-speed values of prostate tumors, in homogeneous background prostate tissue, against comparative synthetic aperture ultrasound reflection techniques.

Figure 3A:
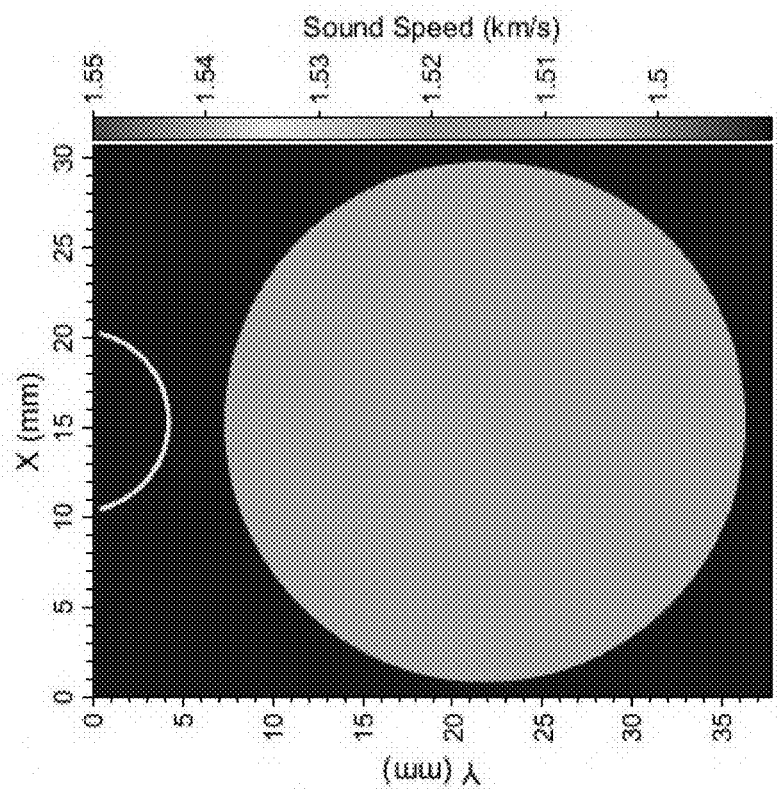
FIGS. 3(a), 3(b), 3(c), and 3(d) illustrate a comparison between sound-speed reconstruction results of ultrasound-waveform inversion using synthetic-aperture ultrasound reflection data in FIG. 3(c) and plane-wave ultrasound reflection data in FIG. 3(d) for a numerical prostate phantom with five tumors in a homogeneous background prostate tissue in FIG. 3(a). Ultrasound-waveform inversion uses the homogeneous sound-speed model of the prostate as the initial model is shown in FIG. 3(c). The white semi-circle is the location of the curved linear transducer array.
Figure 3B:
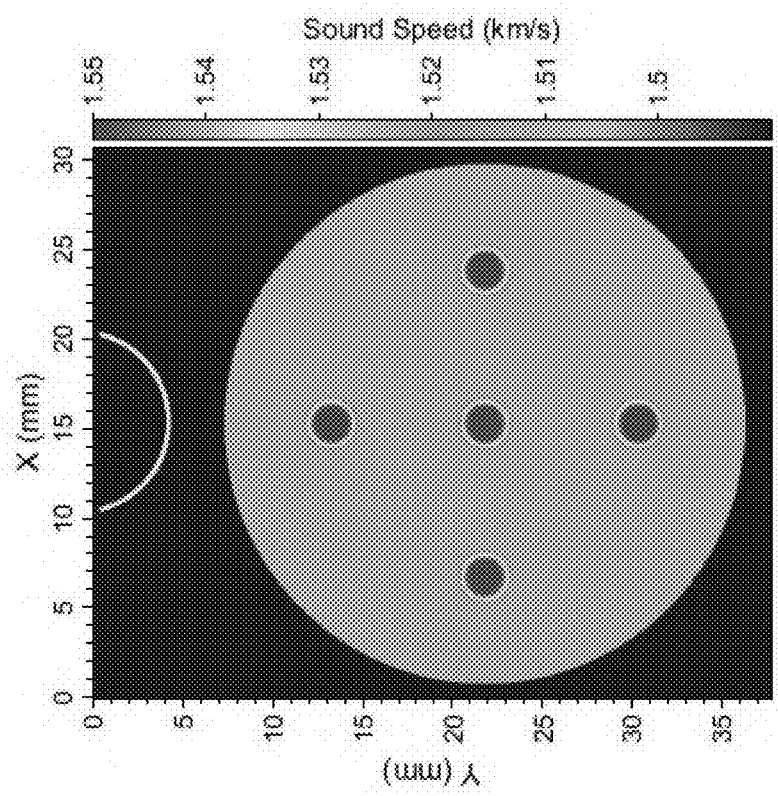
Figure 3D:
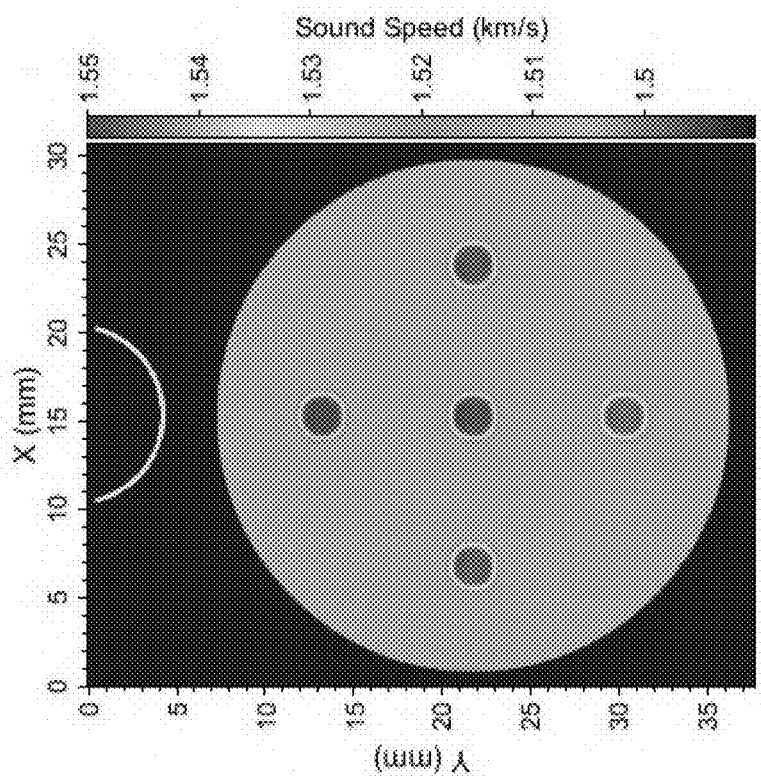
Figure 3C:
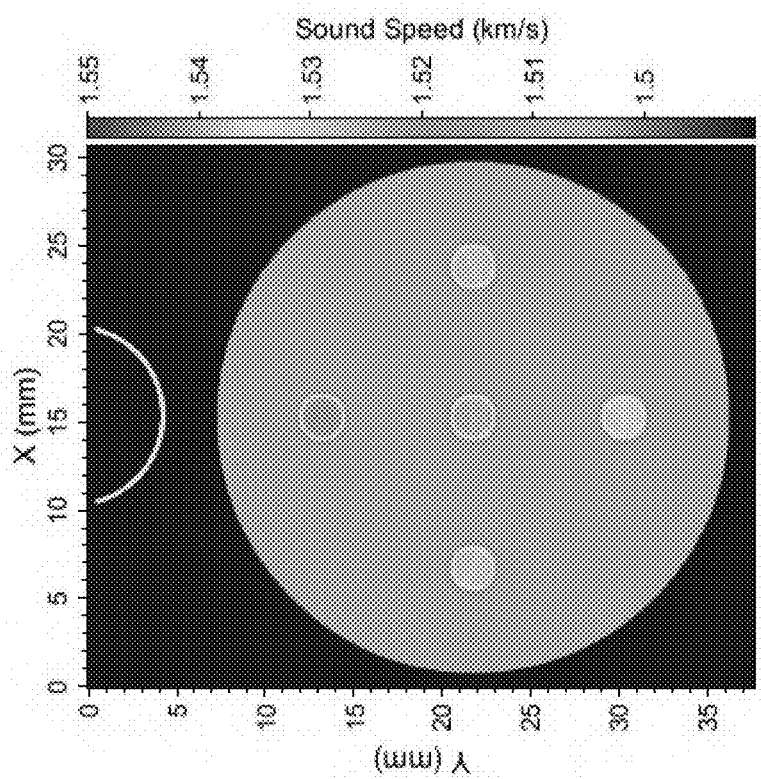

FIGS. 3(a), 3(b), 3(c), and 3(d) illustrate a comparison between sound-speed reconstruction results of ultrasound-waveform inversion using synthetic aperture ultrasound reflection data in FIG. 3(c) and plane-wave ultrasound reflection data in FIG. 3(d) for a numerical (simulated) prostate phantom with five tumors in a homogeneous background prostate tissue in FIG. 3(a). Ultrasound-waveform inversion uses the homogeneous sound-speed model of the prostate as the initial model is shown in FIG. 3(c). The white semi-circle is the location of the curved linear transducer array having a radius of 10.1 mm.

In the following analysis, the prostate tumor margins are assumed to be smooth. Synthetic synthetic-aperture and plane-wave ultrasound reflection data are generated using a high-order finite-difference wave-equation algorithm. For plane-wave full-waveform inversion, plane waves were emitted at 25 different incident angles ranging from −30° to +30° with an angle interval of 2.5°. FIG. 3(b) is the initial sound-speed model for ultrasound-waveform inversion.

FIGS. 3(c) and 3(d) show the sound-speed reconstruction results of performing full-waveform inversion of synthetic aperture ultrasound reflection data and plane-wave ultrasound reflection data, respectively. Comparing the results to the true sound-speed model shown in FIG. 3(a), the plane-wave ultrasound-waveform inversion reconstructs the tumors more accurately than the comparative synthetic aperture ultrasound-waveform inversion.

Figure 4A:
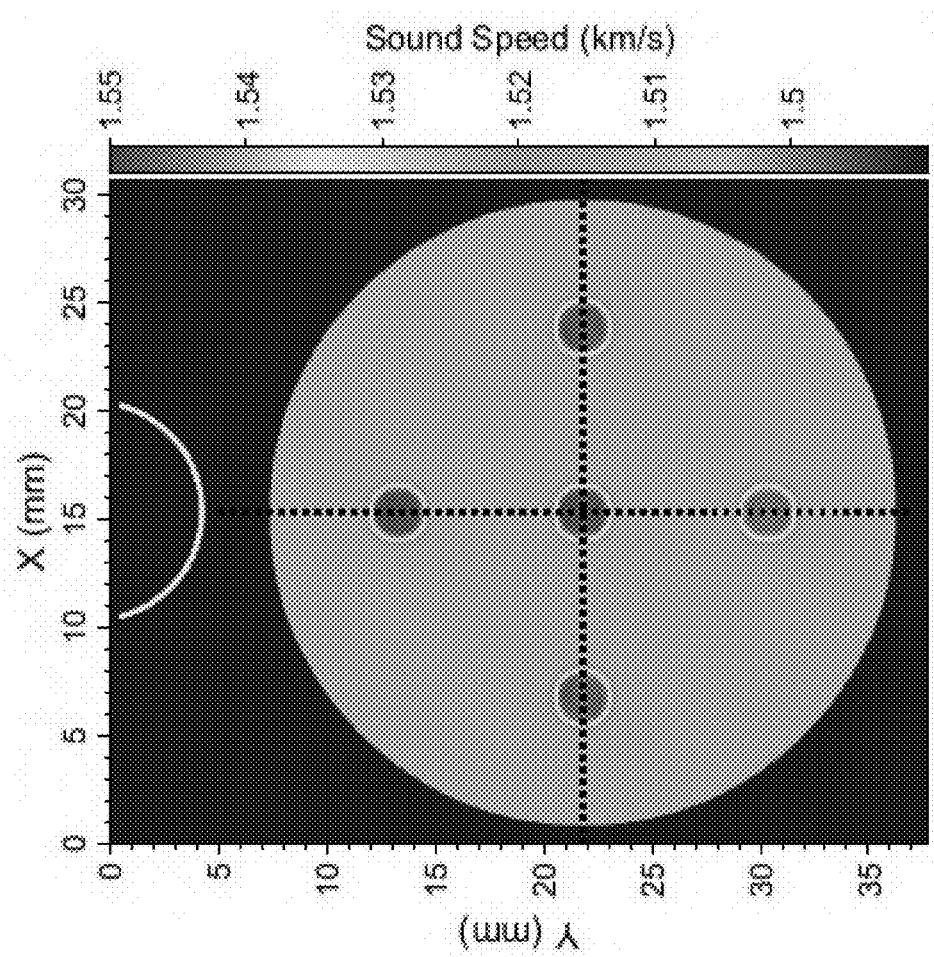
FIGS. 4(a), 4(b), and 4(c) illustrate a comparison of the horizontal (FIG. 4(b)) and vertical (FIG. 4(c)) profiles of ultrasound-waveform inversion results in FIGS. 3(c) and 3(d) for the profile locations in FIG. 4(a).
Figure 4C:
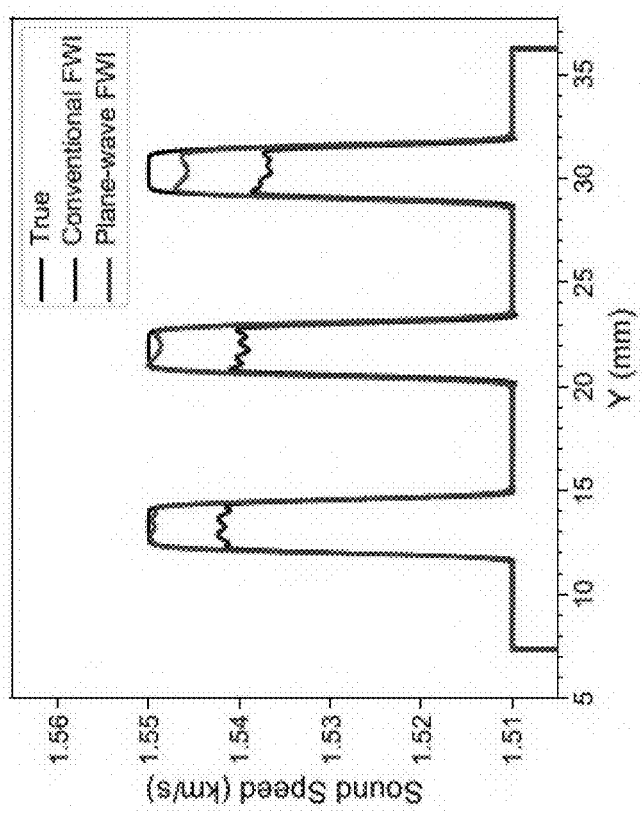
Figure 4B:
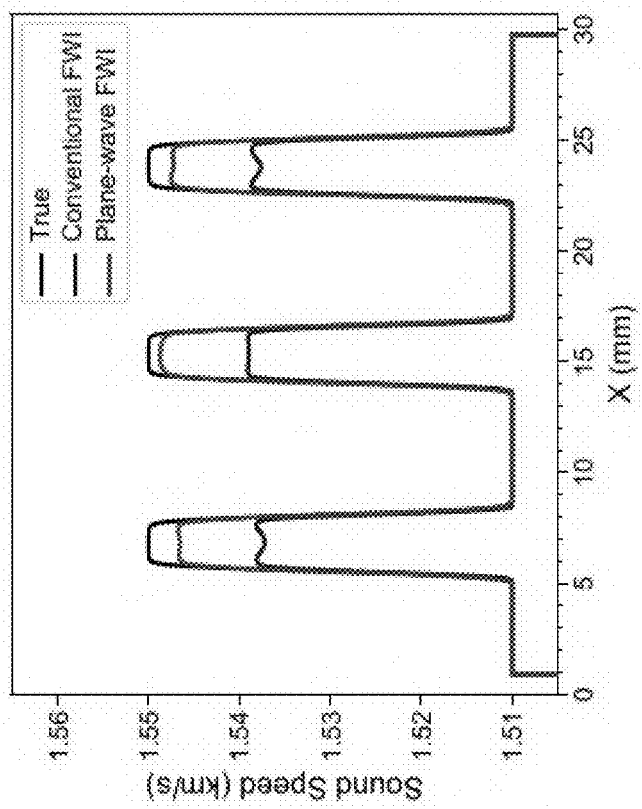

To quantify the comparison between the synthetic aperture ultrasound-waveform inversion and the plane-wave ultrasound-waveform inversion, horizontal and vertical profiles of the inversion results are plotted along the centers of the tumors. FIGS. 4(a), 4(b), and 4(c) illustrate a comparison of the horizontal (FIG. 4(b)) and vertical (FIG. 4(c)) profiles of ultrasound-waveform inversion results in FIGS. 3(c) and 3(d) for the profile locations in FIG. 4(a). FIGS. 4(b) and 4(c) show that plane-wave ultrasound-waveform inversion reconstructs the sound-speed values of the tumors more accurately than synthetic-aperture ultrasound-waveform inversion (e.g., the values are closer to the "True" line than the line for the comparative synthetic aperture ultrasound waveform inversion "Conventional FWI").

Figure 5A:
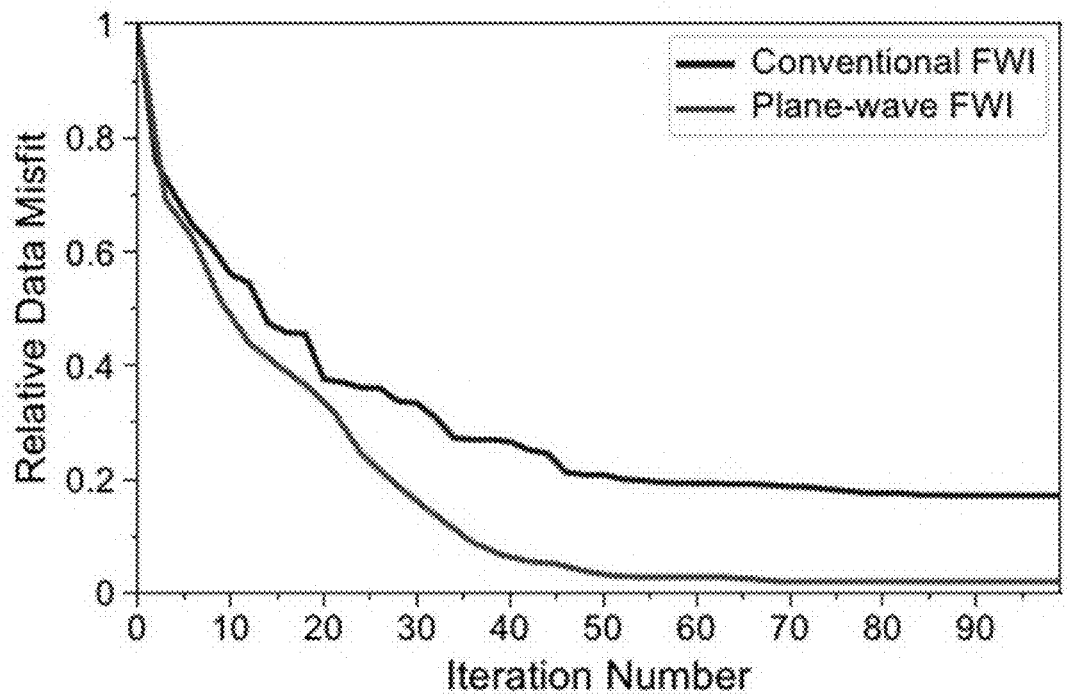
FIGS. 5(a) and 5(b) are graphs illustrating a comparison of the convergence rates of ultrasound-waveform inversion using plane-wave and comparative synthetic-aperture ultrasound data shown in FIGS. 3(d) and 3(c).
Figure 5B:
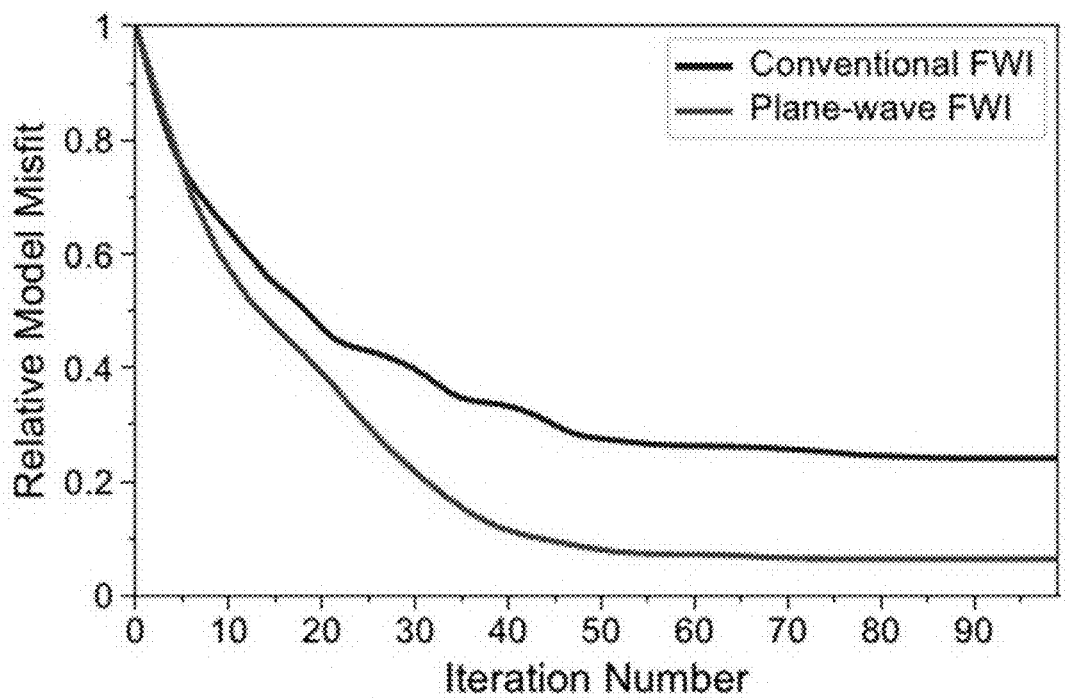

FIGS. 5(a) and 5(b) are graphs illustrating a comparison of the convergence rates of ultrasound-waveform inversion using plane-wave and comparative synthetic-aperture ultrasound data shown in FIGS. 3(d) and 3(c). As shown in FIGS. 5(a) and 5(b), the plane-wave full waveform inversion technique converges more quickly (in fewer iterations) and with less model misfit (e.g., less error) than the comparative synthetic aperture ultrasound waveform inversion.

Numerical analysis was also performed to compare the capability of plane-wave ultrasound-waveform inversion to reconstruct sound-speed values of prostate tumors, in heterogeneous or random background prostate tissue, against comparative synthetic aperture ultrasound reflection techniques.

Figure 6B:
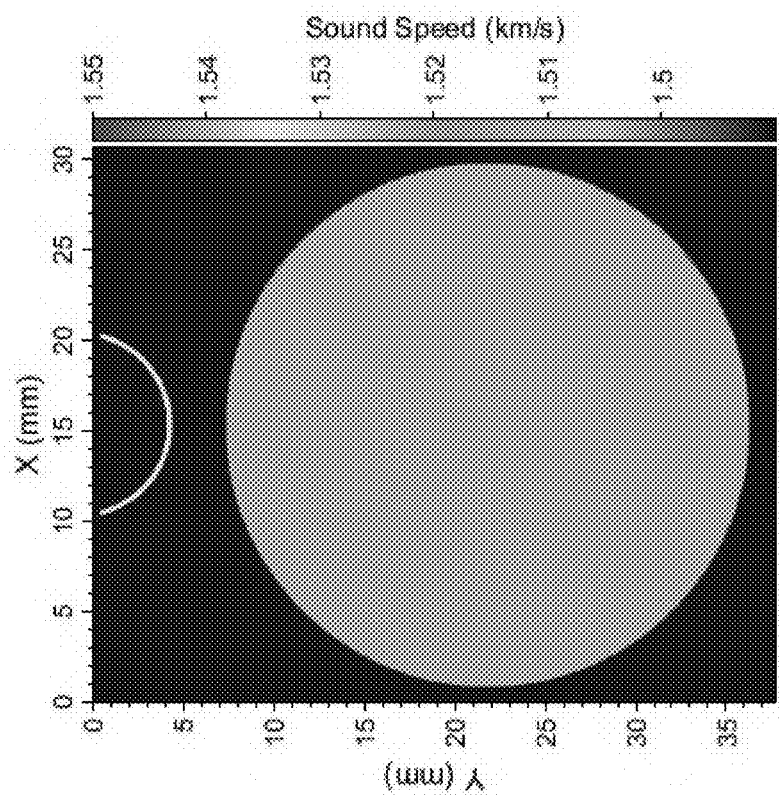
FIGS. 6(a), 6(b), 6(c), and 6(d) illustrate a comparison between sound-speed reconstruction results of full-waveform inversion using synthetic-aperture ultrasound reflection data (FIG. 6(c)) and plane-wave ultrasound reflection data (FIG. 6(d)) for a numerical prostate phantom with five tumors in a random background prostate tissue (FIG. 6(a)). Ultrasound-waveform inversion uses the homogeneous sound-speed model of the prostate as the initial model (FIG. 6(c)). The white semi-circle is the location of the curved linear transducer array.
Figure 6A:
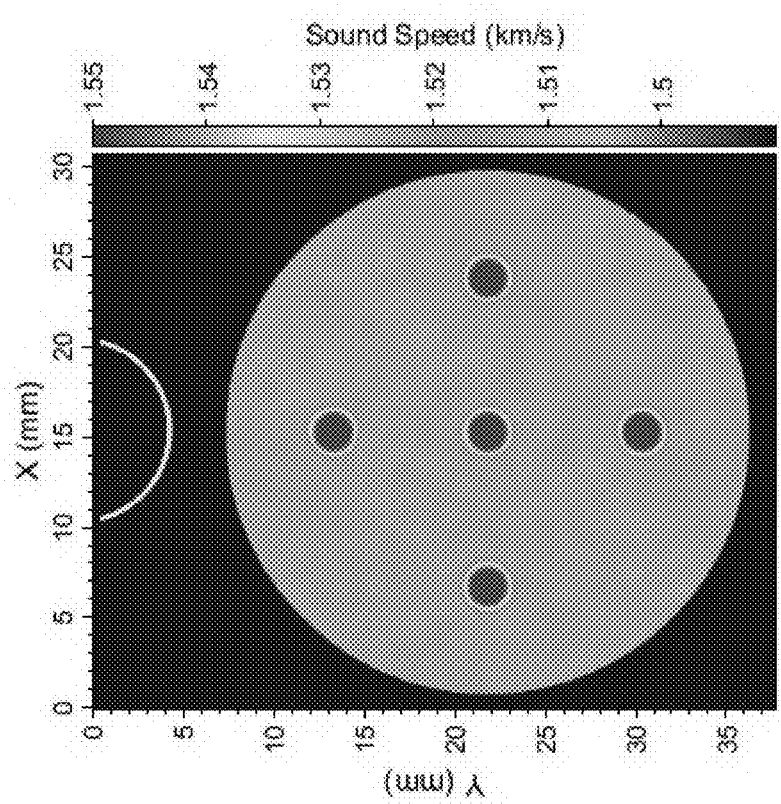
Figure 6D:
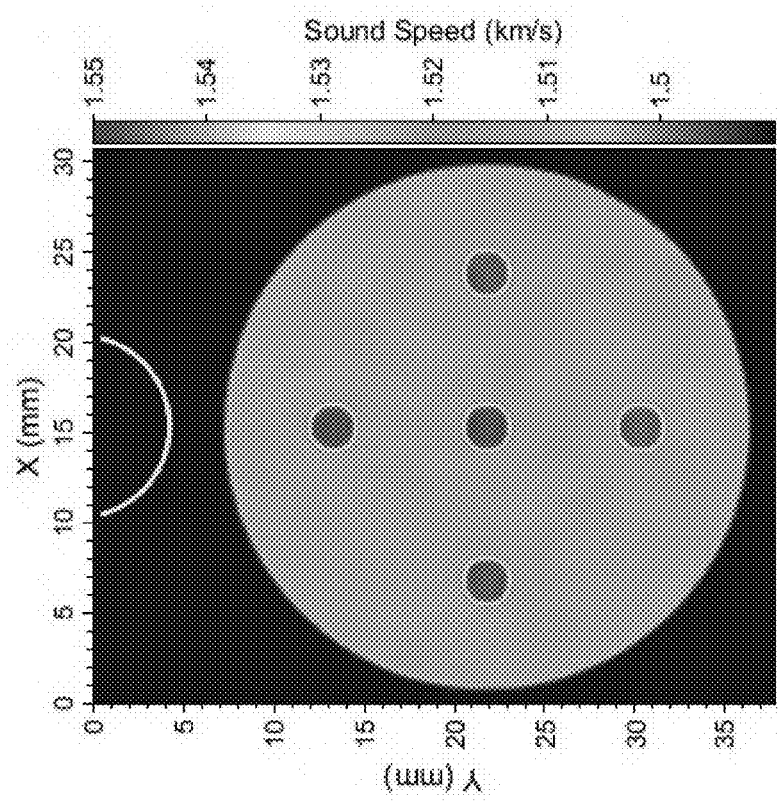
Figure 6C:
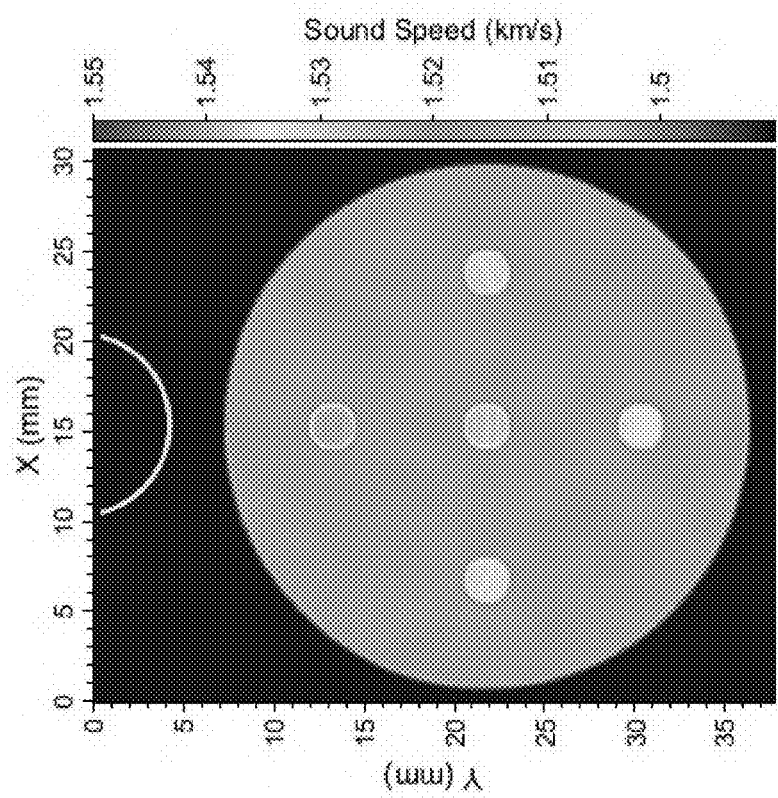

FIGS. 6(a), 6(b). 6(c), and 6(d) illustrate a comparison between sound-speed reconstruction results of full-waveform inversion using synthetic-aperture ultrasound reflection data (FIG. 6(c)) and plane-wave ultrasound reflection data (FIG. 6(d)) for a numerical (simulated) prostate phantom with five tumors in a random background prostate tissue (FIG. 6(a)). Ultrasound-waveform inversion uses the homogeneous sound-speed model of the prostate as the initial model (FIG. 6(c)). The white semi-circle is the location of the curved linear transducer array with a radius of 10.1 mm. The prostate tumors have the same size, shapes, and locations as that in FIG. 3(a). This analysis evaluates the robustness of plane-wave ultrasound-waveform inversion for sound-speed reconstruction of prostate tumors in the heterogeneous prostate. For plane-wave full-waveform inversion, the same number of plane waves was used as in the homogeneous case, discussed above. FIG. 6(b) is the initial sound-speed model for ultrasound-waveform inversion.

FIGS. 6(c) and 6(d) respectively show the sound-speed reconstruction results for the full-waveform inversion of synthetic-aperture ultrasound reflection data and plane-wave ultrasound reflection data. Comparing the results in FIGS. 6(c) and 6(d) with the true sound-speed model in FIG. 6(a), shows that plane-wave ultrasound-waveform inversion still reconstructs the prostate tumors more accurately than synthetic-aperture ultrasound-waveform inversion when the background prostate tissue is heterogeneous.

Figure 7A:
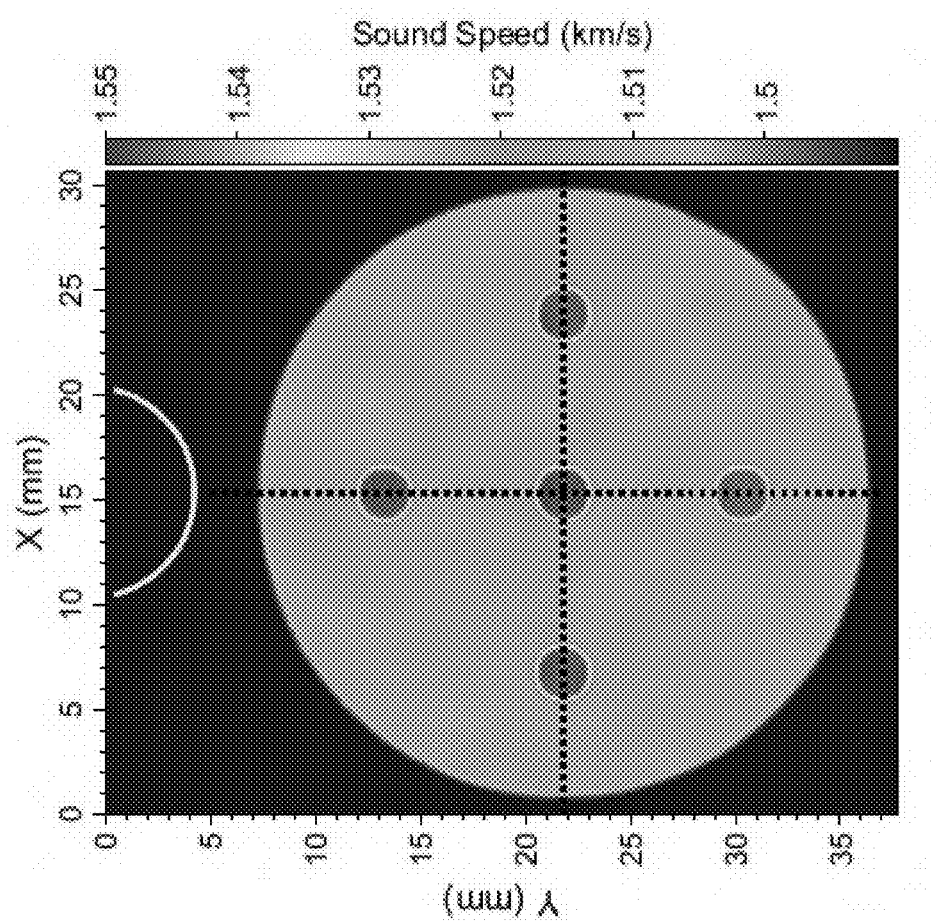
FIGS. 7(a), 7(b), and 7(c) illustrate a comparison of the horizontal (FIG. 7(b)) and vertical (FIG. 7(c)) profiles of ultrasound-waveform inversion results in FIGS. 6(c) and 6(d) for the profile locations in FIG. 7(a).
Figure 7C:
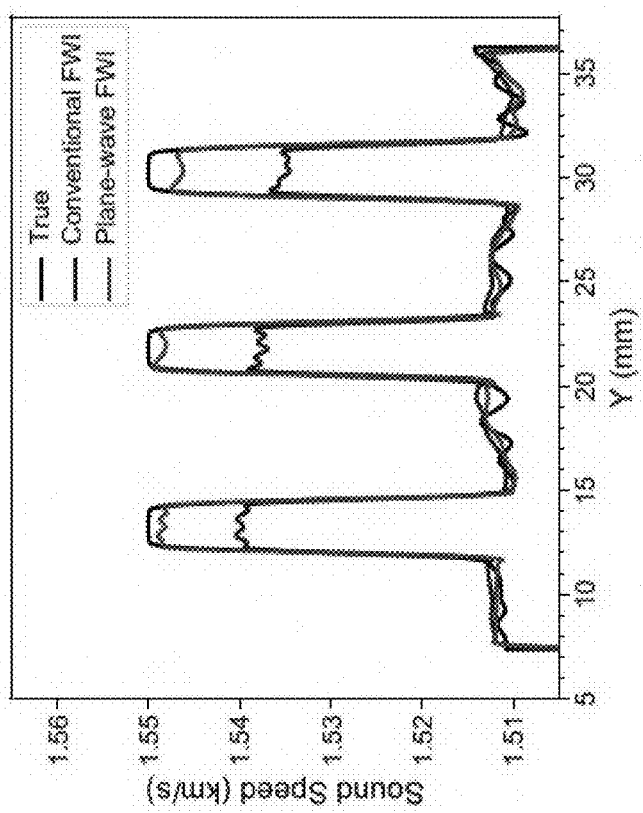
Figure 7B:
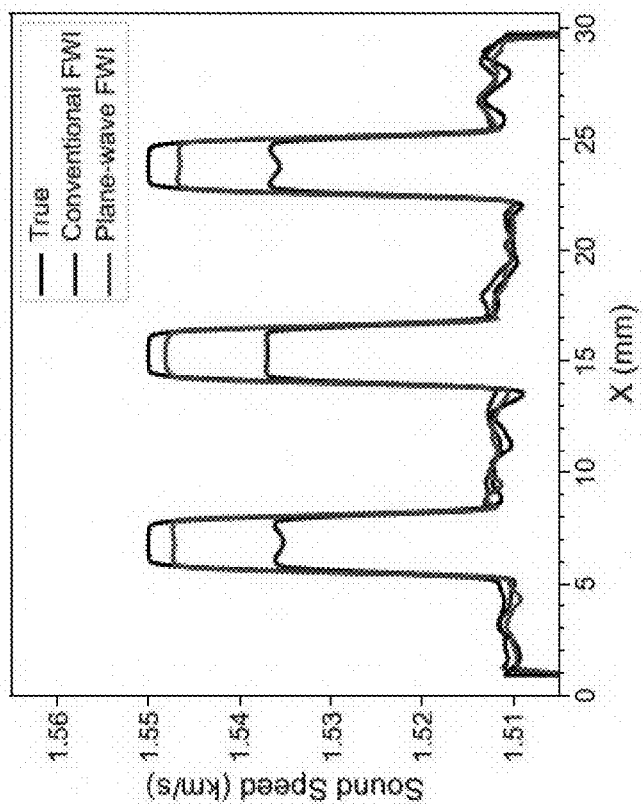

FIGS. 7(a), 7(b), and 7(c) illustrate a quantitative comparison of the horizontal (FIG. 7(b)) and vertical (FIG. 7(c)) profiles of ultrasound-waveform inversion results in FIGS. 6(c) and 6(d) for the profile locations in FIG. 7(a). As the homogeneous case, FIGS. 7(b) and 7(c) show that plane-wave ultrasound-waveform inversion can more accurately reconstruct the tumor sound-speed values than the comparative synthetic-aperture ultrasound-waveform inversion when the tumors are in heterogeneous background prostate tissue.

Figure 8B:
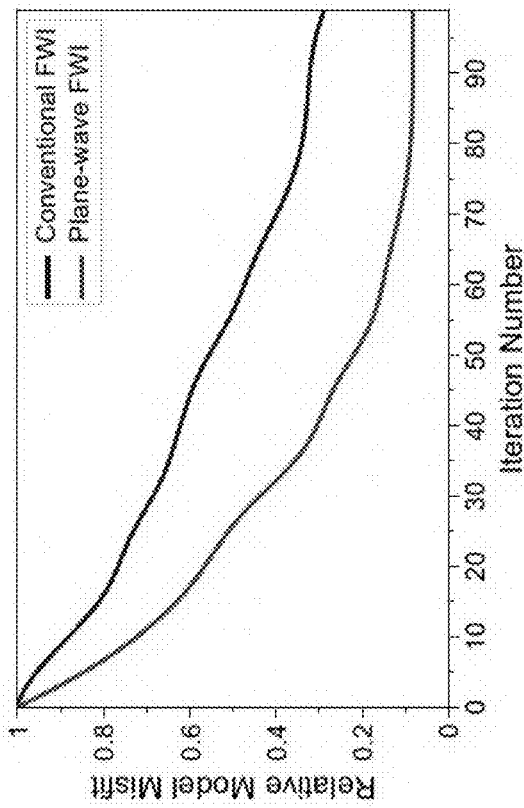
FIGS. 8(a) and 8(b) illustrate a comparison of the convergence rates of ultrasound-waveform inversion using plane-wave and comparative synthetic-aperture ultrasound data shown in FIGS. 6(d) and 6(c).
Figure 8A:
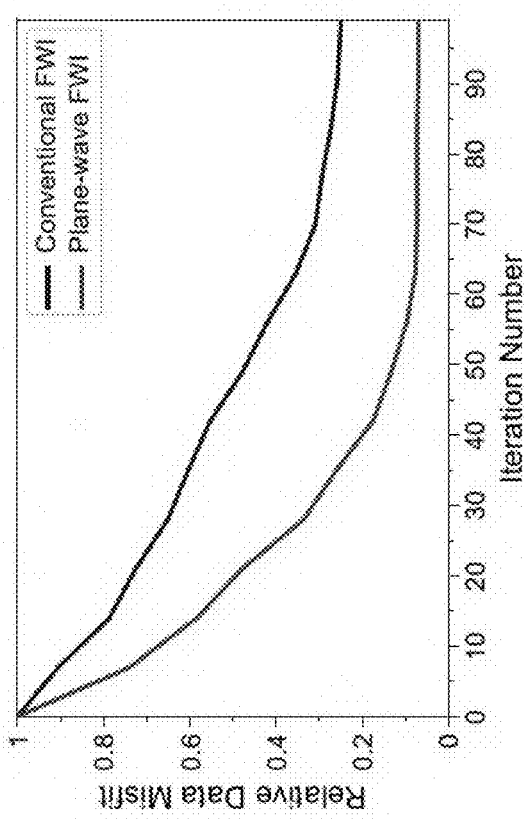

FIGS. 8(a) and 8(b) illustrate a comparison of the convergence rates of ultrasound-waveform inversion using plane-wave and comparative synthetic-aperture ultrasound data shown in FIGS. 6(d) and 6(c). Similar to the homogeneous case, the convergence rates of ultrasound-waveform inversion using plane-wave and comparative synthetic-aperture ultrasound data as shown in FIG. 8 demonstrate that plane-wave ultrasound-waveform inversion converges more quickly (e.g., in fewer iterations) and better (with less misfit) than that using the comparative synthetic-aperture ultrasound data.

Figure 9:
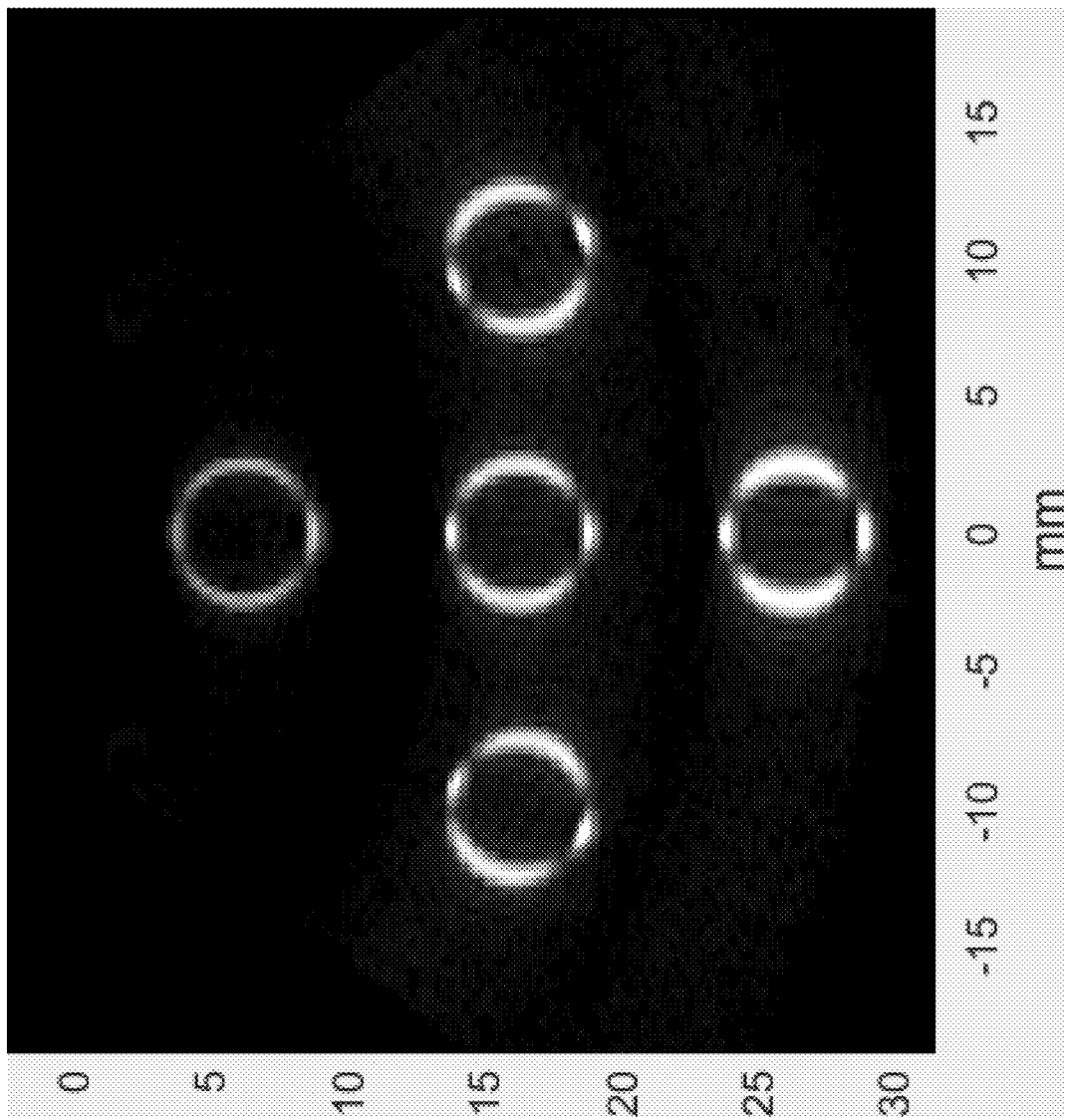
FIG. 9 is a simulated image obtained using Verasonics® plane-wave imaging with 33 plane waves illuminating the target imaging region with five lesions.

FIG. 9 is a simulated image obtained using Verasonics® plane-wave imaging with 33 plane waves illuminating the target imaging region with five lesions.

The simulated image shown in FIG. 9 was computed from a transrectal ultrasound tomography system according to one embodiment of the present invention using plane-wave imaging with 33 plane waves. The image resolution decreases with the depth, as expected. Nevertheless, the system can clearly image the five lesions. These lesion locations can be used as a prior spatial information for plane-wave ultrasound-waveform inversion to improve sound-speed reconstruction results of prostate tumors.

Figure 10:
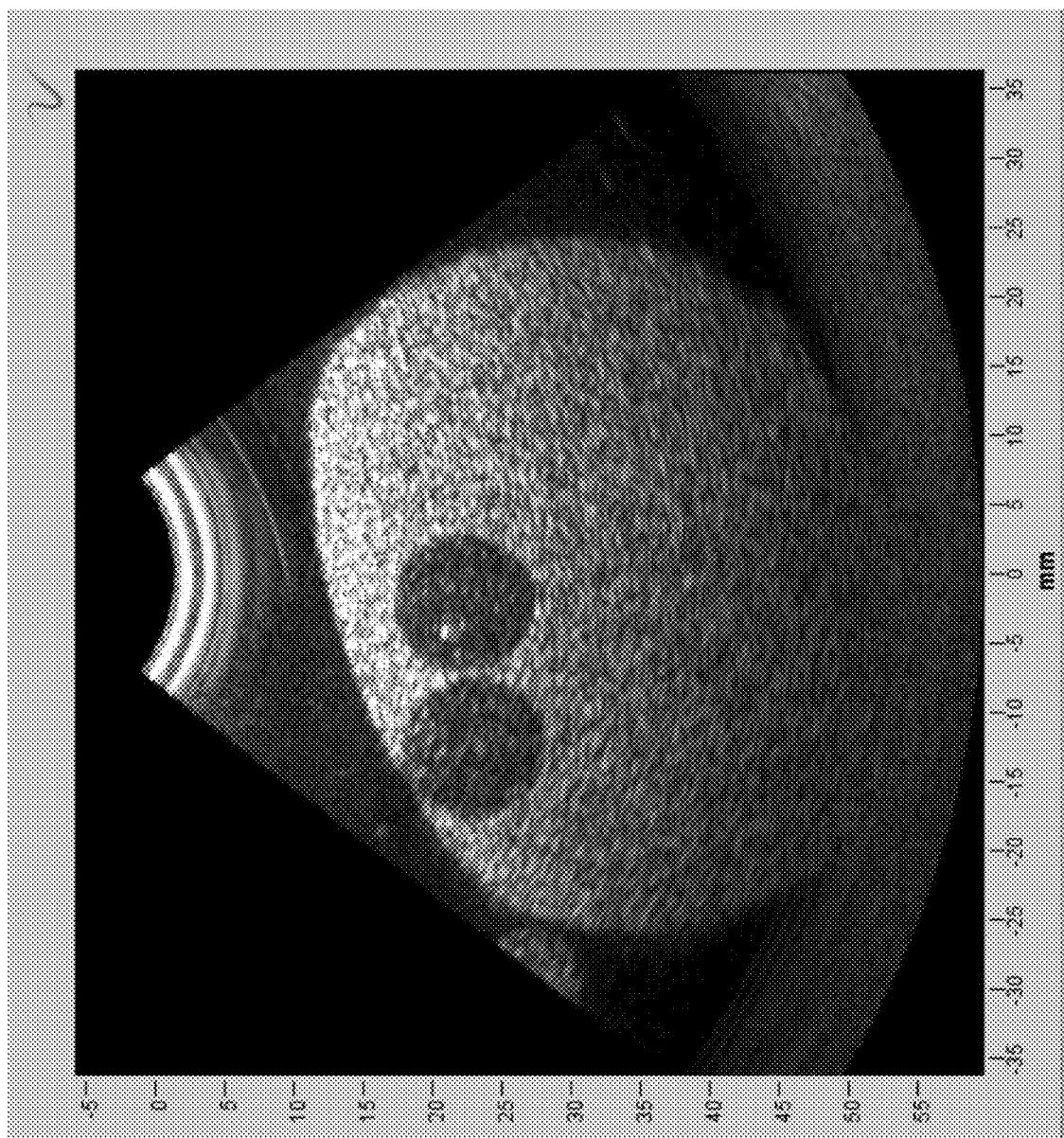
FIG. 10 is a plane-wave ultrasound image of a tissue-mimicking prostate phantom obtained according to one embodiment of the present invention using a Verasonics® plane-wave imaging system with 11 plane waves illuminating the imaging region.

FIG. 10 is a plane-wave ultrasound image for a tissue-mimicking (physical) prostate phantom obtained in accordance with one embodiment of the present invention using 11 plane waves emitted using a Verasonics® plane-wave imaging system. The two prostate tumors are clearly imaged, thereby illustrating the effectiveness of techniques in accordance with embodiments of the present invention.

Figure 11:
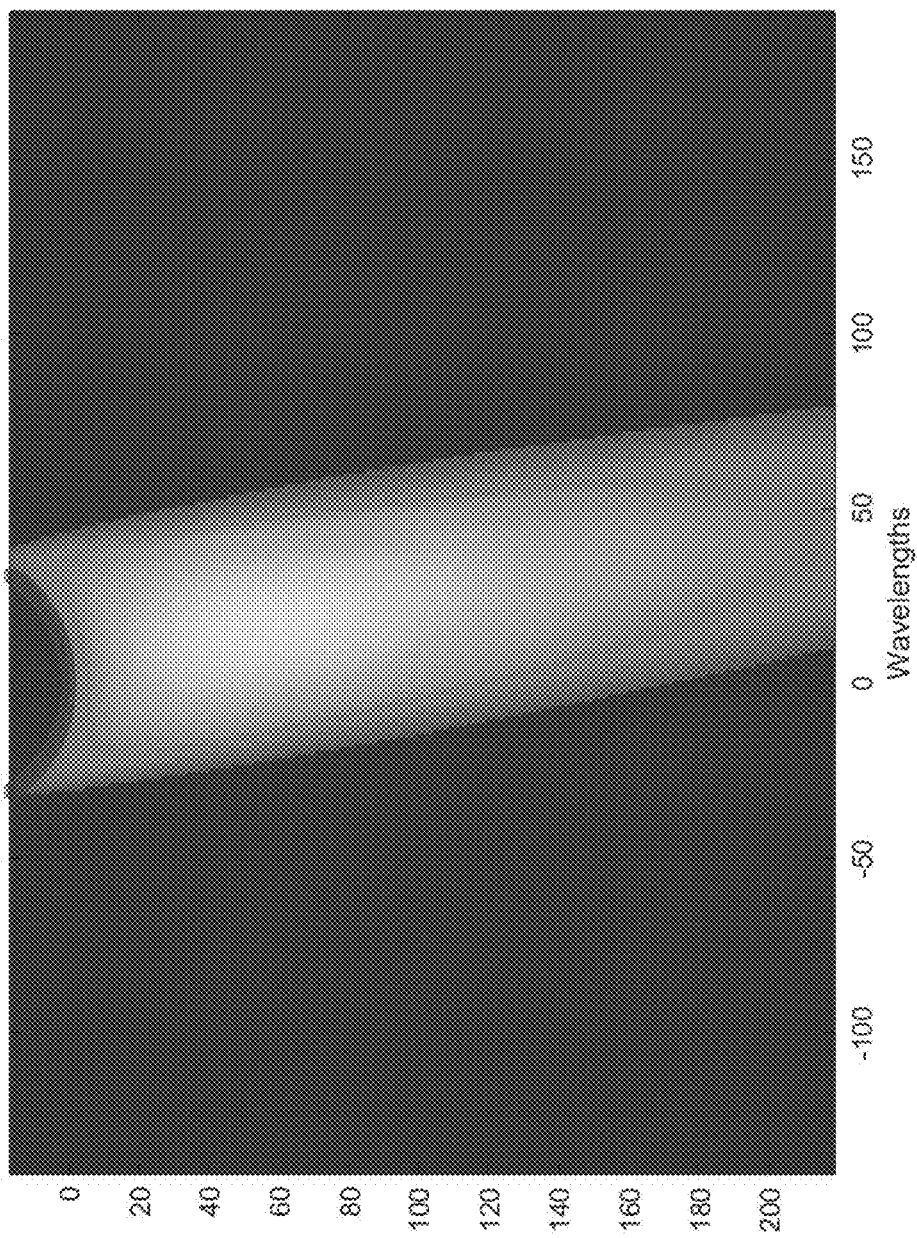
FIG. 11 is an illumination map for one data acquisition angle associated with a plane-wave imaging system according to one embodiment of the present invention.
Figure 12:
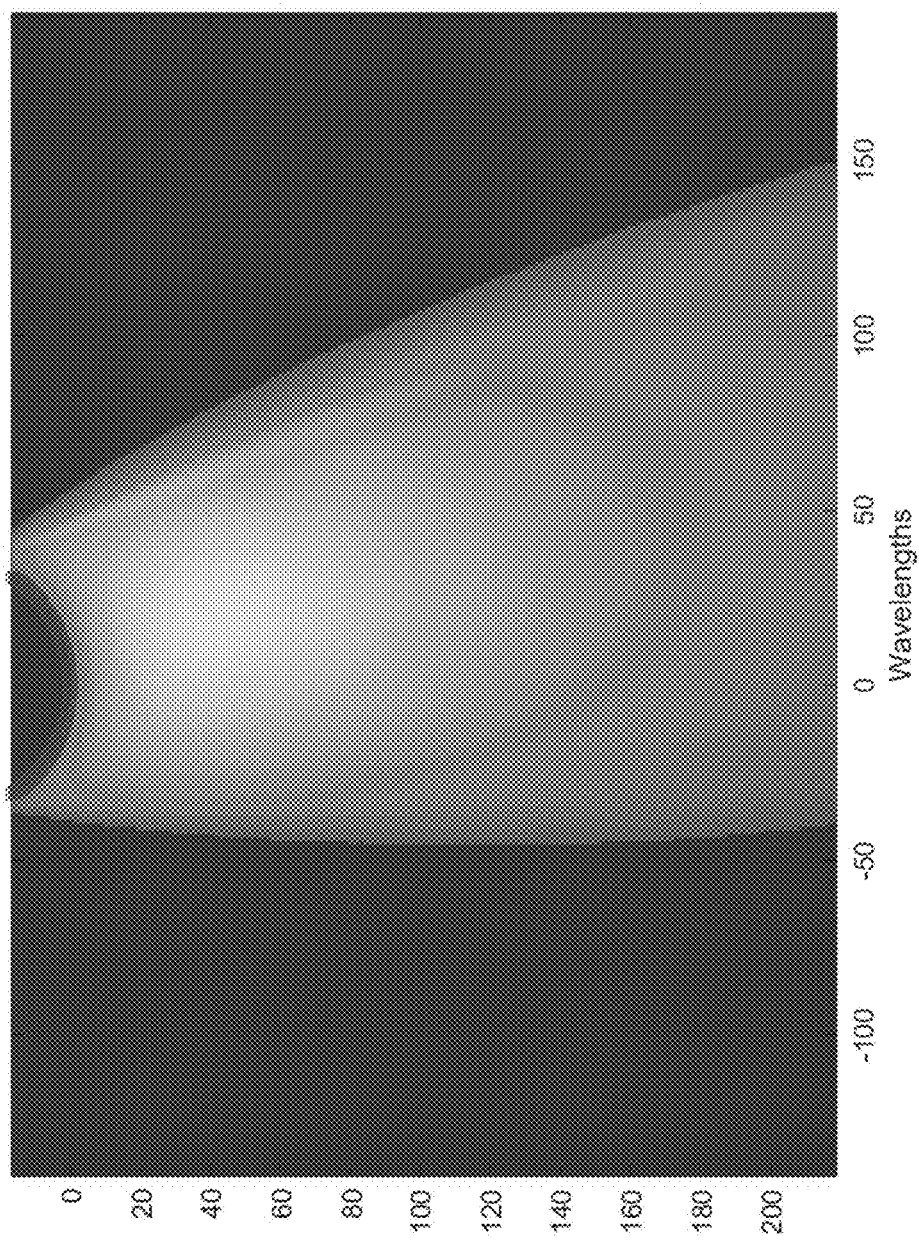
FIG. 12 is an illumination map for one data acquisition angle associated with a fan-beam imaging system according to one embodiment of the present invention.
Figure 13:
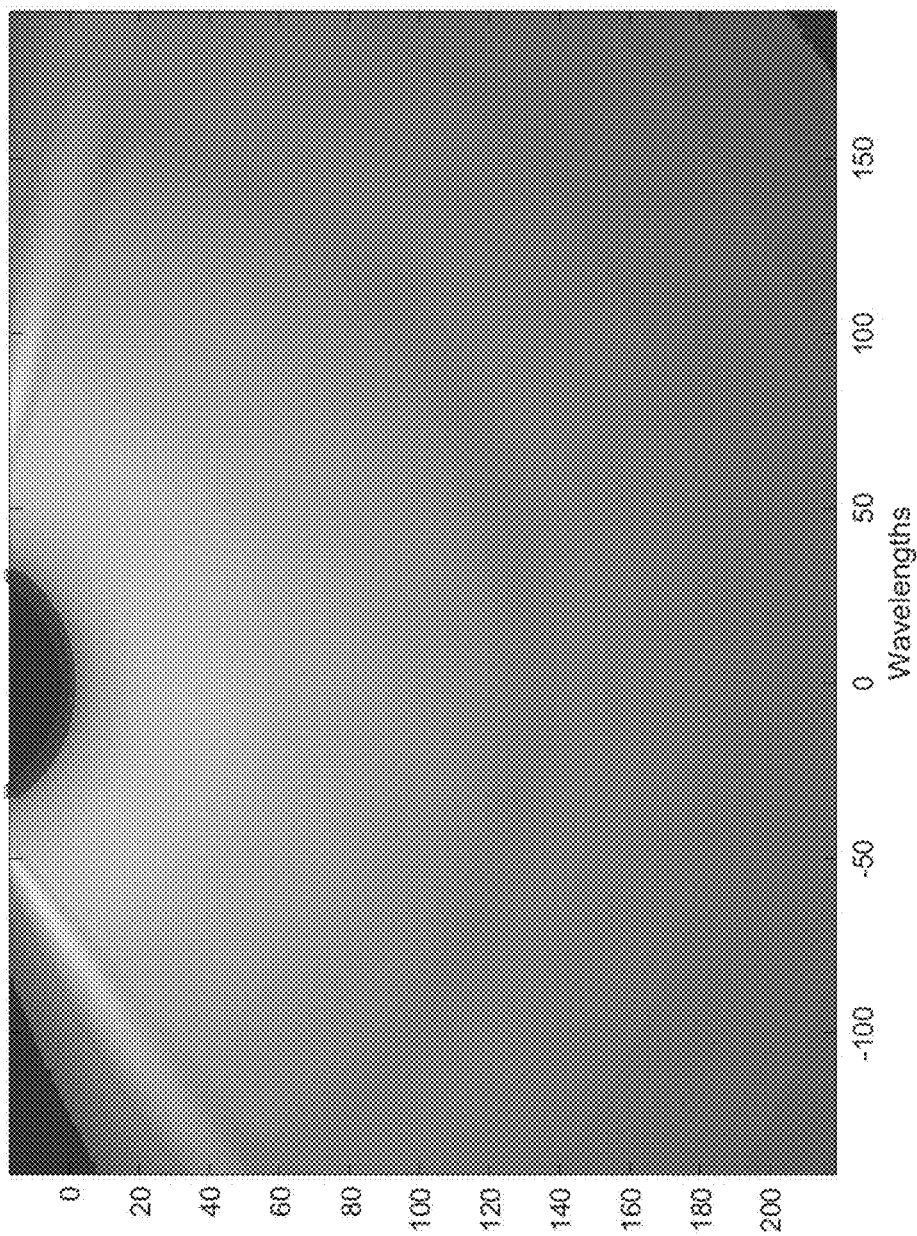
FIG. 13 is an illumination map for one data acquisition angle associated with a wide-beam imaging system according to one embodiment of the present invention.

FIG. 11, FIG. 12 and FIG. 13 are illumination maps for one data acquisition angle associated with plane-wave, fan-beam, and wide-beam imaging systems, respectively. On these three maps, the blue color represents low illumination while yellow color represents high illumination. The red dotted curves at the top of FIGS. 11, 12, and 13 represent the position of the intracavitary curved linear array 300 for acquiring transrectal plane-wave, fan-beam or wide-beam ultrasound reflection data, respectively.

Figure 14:
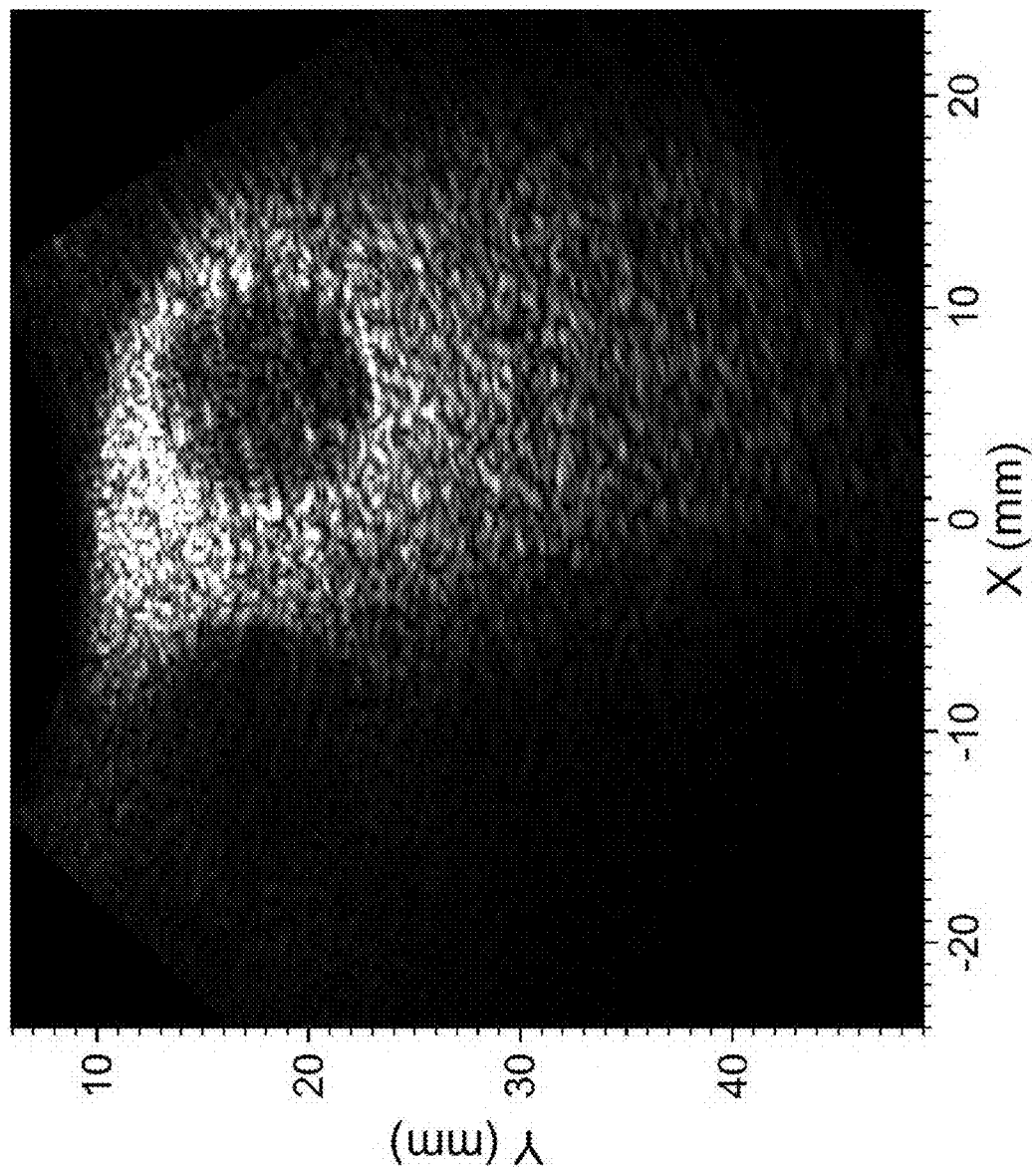
FIG. 14 is an ultrasound image obtained at one illumination angle using a plane-wave imaging system according to one embodiment of the present invention.
Figure 15:
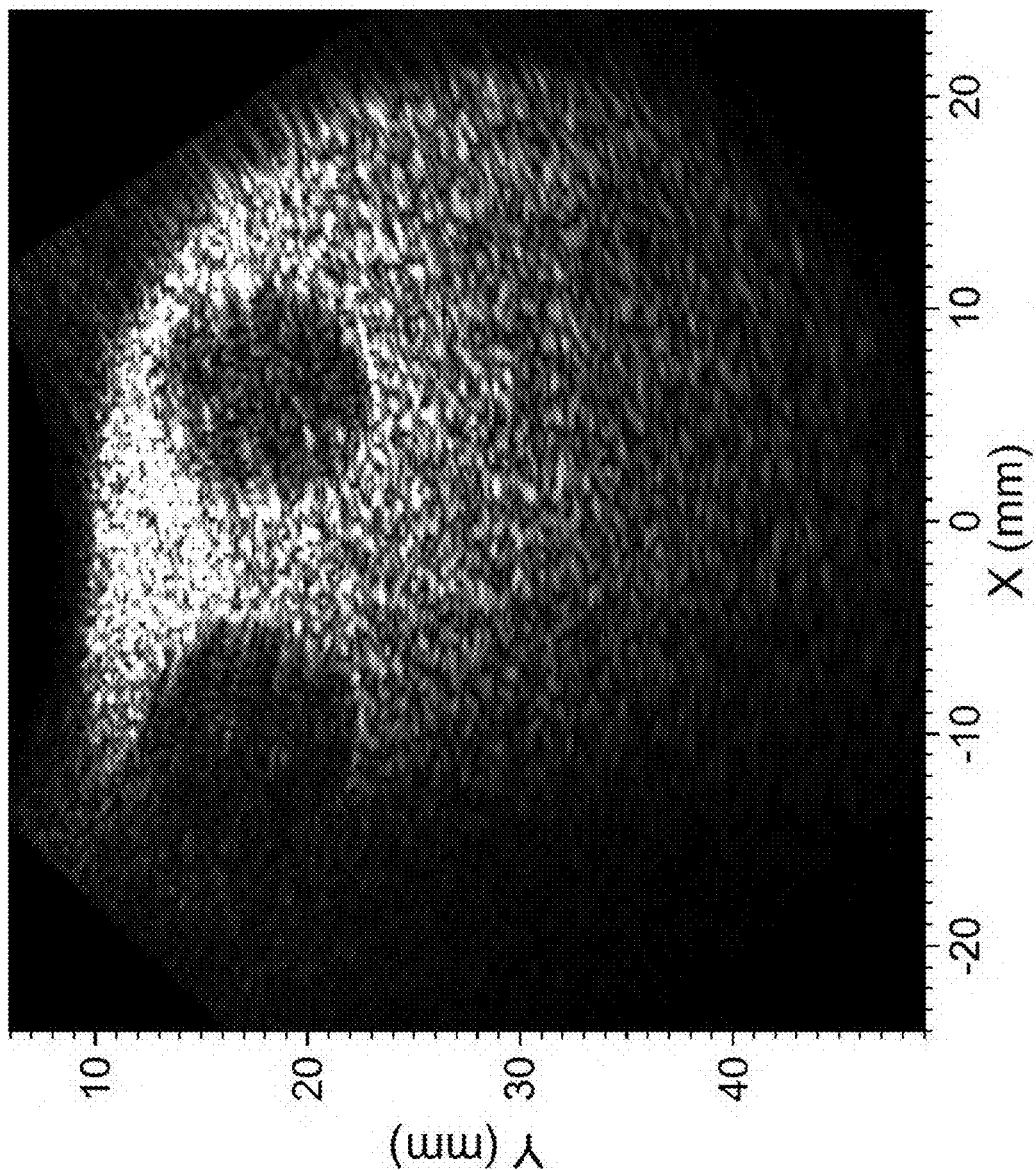
FIG. 15 is an ultrasound image obtained at one illumination angle using a fan-beam imaging system according to one embodiment of the present invention.
Figure 16:
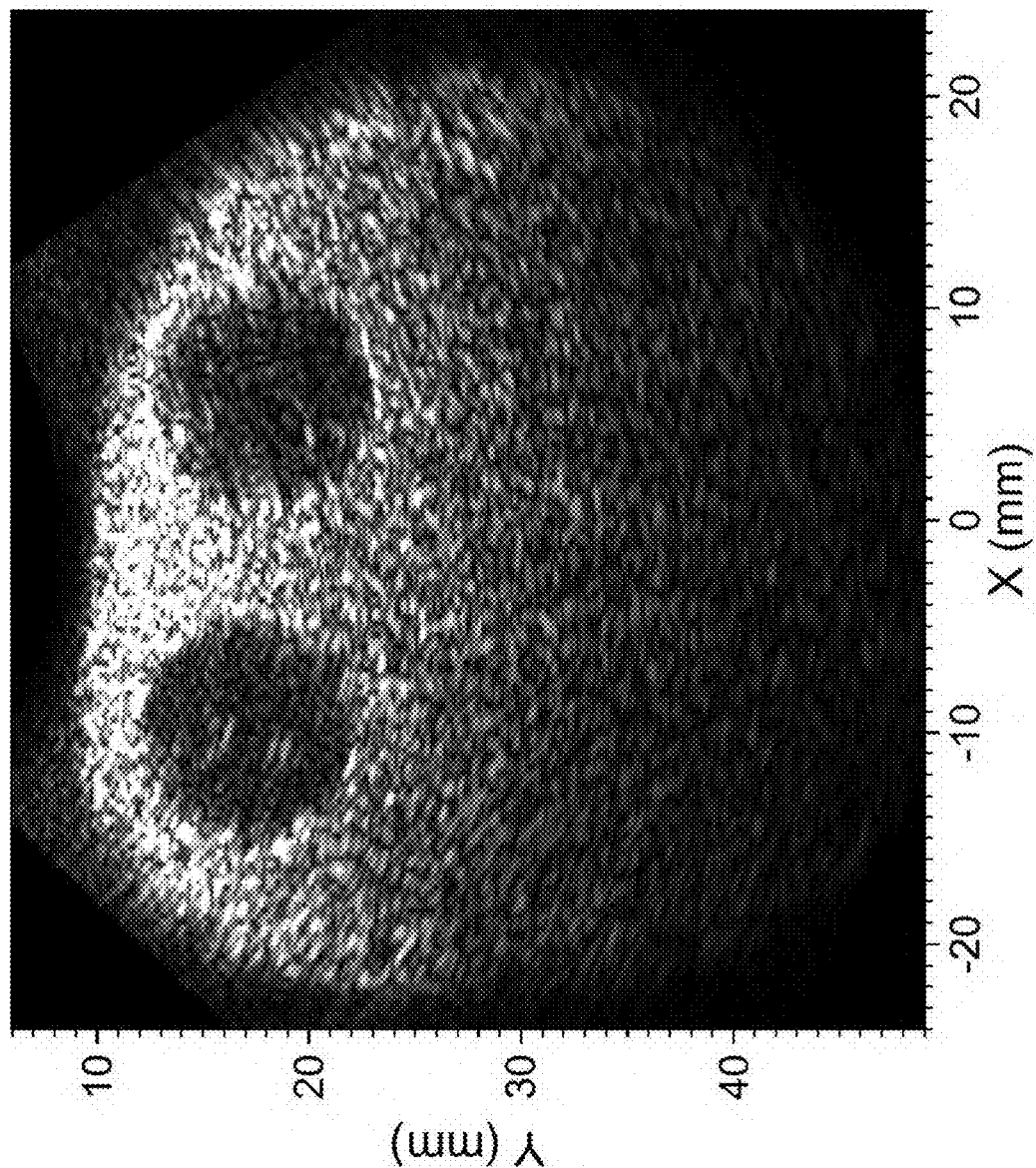
FIG. 16 is an ultrasound image obtained at one illumination angle using a wide-beam imaging system according to one embodiment of the present invention.

FIG. 14, FIG. 15 and FIG. 16 are ultrasound images obtained using, respectively, plane-wave, fan-beam and wide-beam imaging systems for one illumination angle, according to some embodiments of the present invention. These three images correspond to the three illumination maps shown in FIG. 11, FIG. 12 and FIG. 13, respectively. These ultrasound images show that wider illumination leads to wider imaging range. A final ultrasound image is obtained by stacking ultrasound images from all illumination angles.

Figure 17:
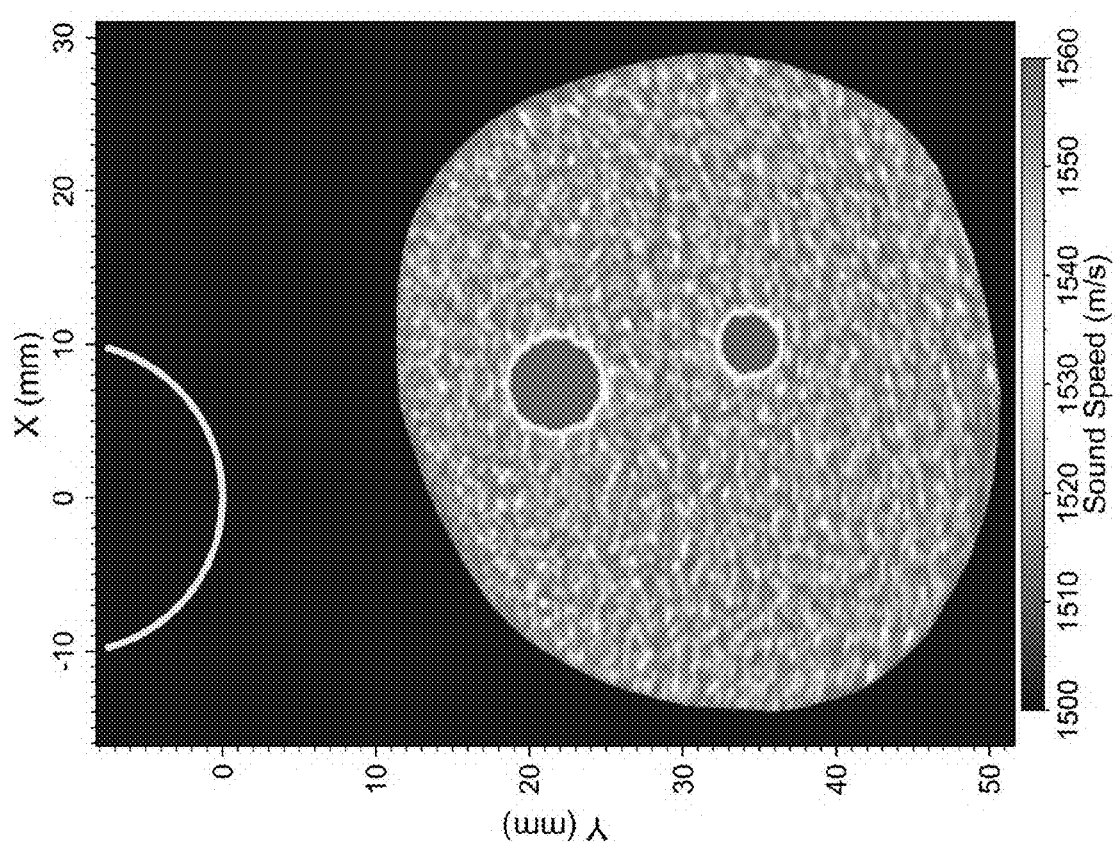
FIG. 17 depicts an ultrasound image of a prostate phantom model with two sound speed anomalies mimicking two tumors.

FIG. 17 is a prostate phantom model with two sound speed anomalies mimicking two tumors. The random sound speed variations in the background mimics human tissue. The yellow curve at the right-top of the Figure represents the position of the intracavitary curved linear array 300 for acquiring transrectal plane-wave, fan-beam or wide-beam ultrasound reflection data.

Figure 18:
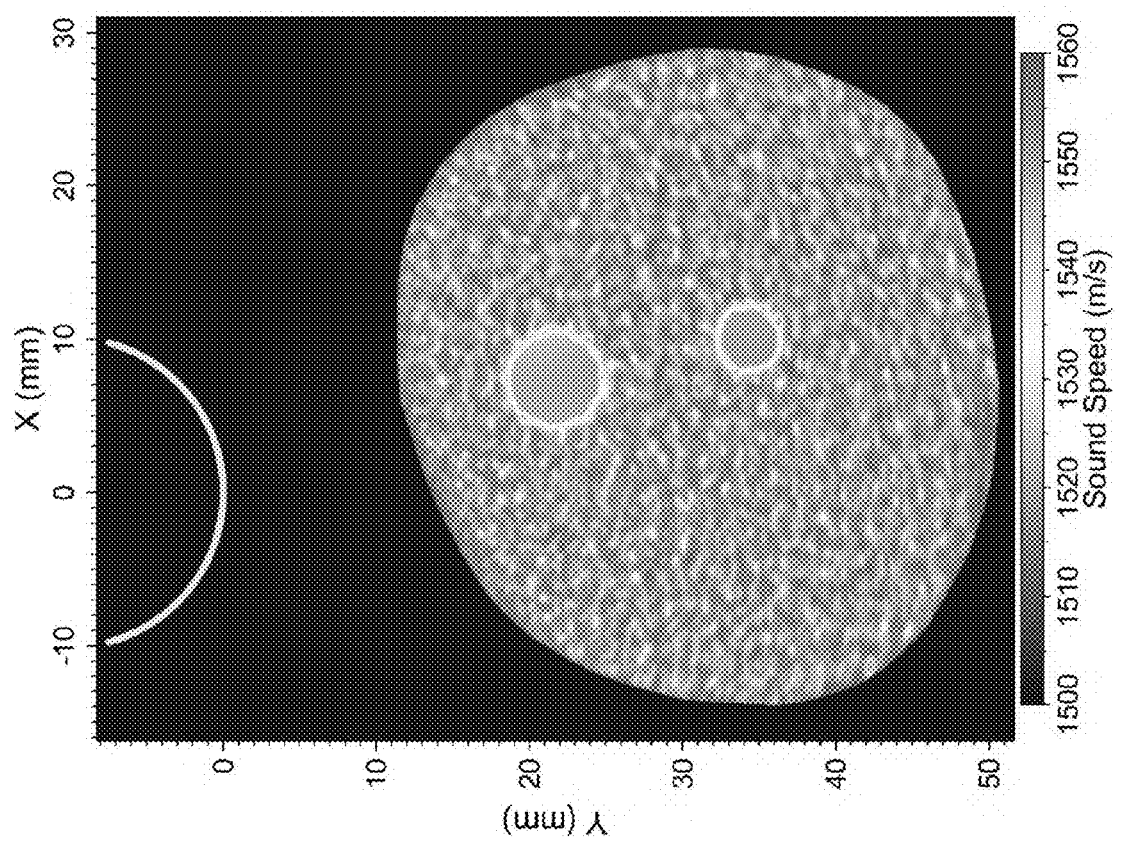
FIG. 18 depicts the prostate phantom sound speed model of FIG. 17 reconstructed using a plane-wave imaging system according to one embodiment of the present invention.

FIG. 18 is the prostate phantom sound speed model reconstructed using the plane-wave imaging system. The reconstructed sound speed model shows that the plane-wave ultrasound-waveform inversion method according to one embodiment of the present invention recovers the sound speed anomalies of the two tumors.

Figure 19:
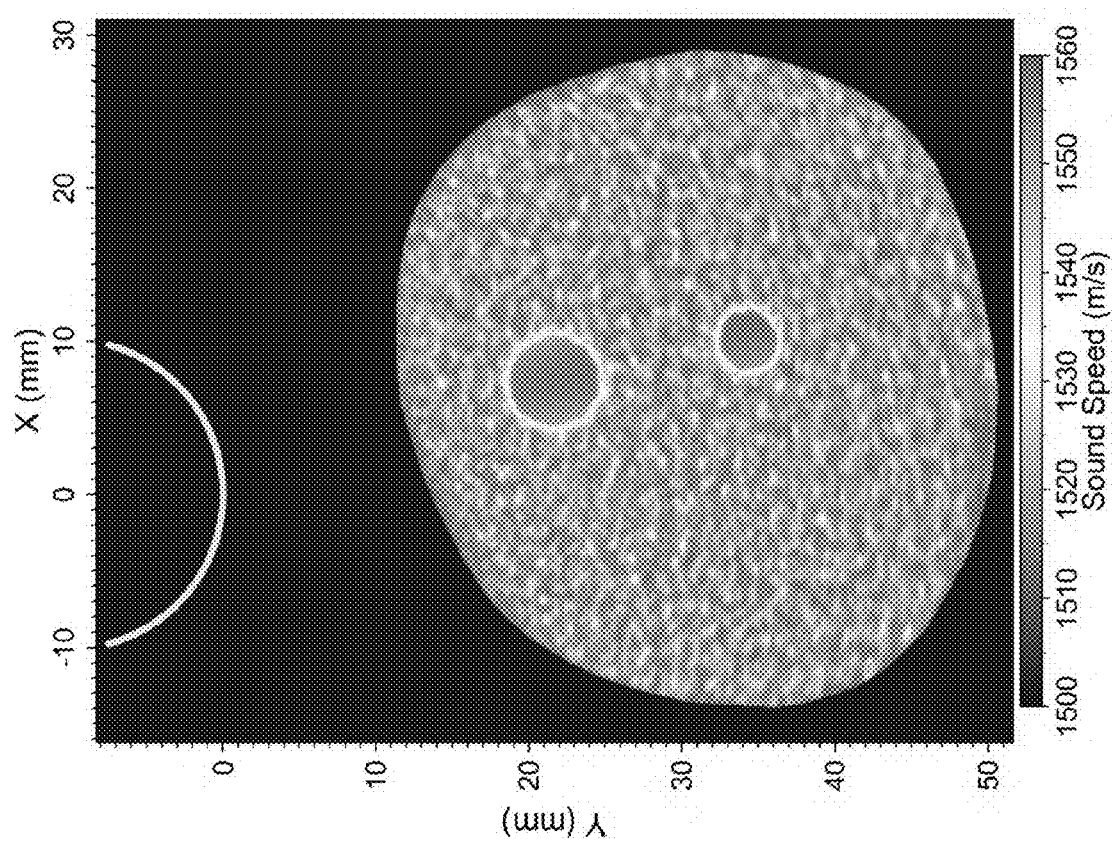
FIG. 19 depicts the prostate phantom sound speed model reconstructed using a fan-beam imaging system according to one embodiment of the present invention.

FIG. 19 is the prostate phantom sound speed model reconstructed using the fan-beam imaging system. The reconstructed sound speed model shows that the fan-beam ultrasound-waveform inversion method according to one embodiment of the present invention recovers the sound speed anomalies of the two tumors. In addition, the reconstructed sound speed anomalies by the fan-beam ultrasound-waveform inversion are closer to the true sound speed anomalies shown in FIG. 17 compared with that obtained by the plane-wave ultrasound-waveform inversion method.

Accordingly, aspects of embodiments of the present invention relate to a transrectal ultrasound tomography system. One example embodiment of a system includes a Verasonics Vantage 256 system and a GE intracavitary curved linear array for acquiring transrectal plane-wave ultrasound reflection data. A plane-wave ultrasound-waveform inversion algorithm according to embodiments of the present invention accurately reconstructs sound-speed values of prostate tumors using ultrasound reflection data. Numerical results demonstrate that using transrectal plane-wave ultrasound reflection data and plane-wave ultrasound-waveform inversion algorithm according to embodiments of the present invention can more accurately reconstruct sound-speed values of prostate tumors than the comparative synthetic-aperture ultrasound-waveform inversion. Transrectal ultrasound tomography systems and plane-wave ultrasound-waveform inversion algorithms according to embodiments of the present invention enable transrectal ultrasound tomography for prostate cancer imaging and characterization.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A system for plane-wave or fan-beam ultrasound tomography comprising:
  a linear or curved linear ultrasound transducer array comprising a plurality of transducers;
  a multi-channel ultrasound array controller configured to control the linear ultrasound transducer array;
  a host controller comprising a processor and memory, the memory storing instructions that, when executed by the processor, cause the processor to:
  control the multi-channel ultrasound array controller to control the linear ultrasound transducer array to emit plane-wave or fan-beam ultrasound into a biological tissue;
  receive plane-wave or fan-beam ultrasound waveform data from the transducers, the plane-wave or fan-beam ultrasound waveform data comprising reflections of the plane-wave or fan-beam ultrasound from the biological tissue;
  compute a synthetic ultrasound-waveform inversion from the received plane-wave or fan-beam ultrasound waveform data; and
  compute an image of the biological tissue from the synthetic ultrasound-waveform inversion,
  wherein the memory further stores instructions that, when executed by the processor of the host controller, cause the host controller to compute the ultrasound waveform inversion by iteratively minimizing a plane-wave or fan-beam misfit function:

$$\chi(m) = \sum_{t,s,r} \frac{1}{2} \|d - f(m)\|_2^2,$$

where d is the plane-wave or fan-beam ultrasound waveform data and f(m) is an iteration of a synthetic ultrasound-waveform inversion, m is a physical parameter model, and a data misfit is accumulated for all recording time (t) of the waveform, all the transducers (s) and all the receivers (r), and where the computed synthetic ultrasound-waveform inversion corresponds to the iteration of the synthetic ultrasound-waveform inversion that minimizes $\chi(m)$.

2. The system of claim 1, wherein the physical parameter model m comprises sound speed values, density values, and attenuation values.

3. A system for plane-wave or fan-beam ultrasound tomography comprising:
  a linear or curved linear ultrasound transducer array comprising a plurality of transducers;
  a multi-channel ultrasound array controller configured to control the linear ultrasound transducer array;
  a host controller comprising a processor and memory, the memory storing instructions that, when executed by the processor, cause the processor to:
  control the multi-channel ultrasound array controller to control the linear ultrasound transducer array to emit plane-wave or fan-beam ultrasound into a biological tissue;
  receive plane-wave or fan-beam ultrasound waveform data from the transducers, the plane-wave or fan-beam ultrasound waveform data comprising reflections of the plane-wave or fan-beam ultrasound from the biological tissue;
  compute a synthetic ultrasound-waveform inversion from the received plane-wave or fan-beam ultrasound waveform data; and
  compute an image of the biological tissue from the synthetic ultrasound-waveform inversion,
  wherein the memory further stores instructions that, when executed by the processor of the host controller, cause the host controller to compute the ultrasound waveform inversion by iteratively minimizing a plane-wave or fan-beam misfit function:

$$\chi(m) = \sum_{t,s',r} \frac{1}{2} \left\| \sum_i^s d_i(\Delta t_i, p_j) - \sum_i^s f_i(m, \Delta t_i, p_j) \right\|_2^2$$

where s' is the number of plane-wave or fan-beam gathers, $d_i$ and $f_i$ are an i-th single-point received ultrasound waveform data and an i-th synthetic ultrasound-waveform inversion data gather of, respectively, a plurality of gathers of received ultrasound data and a plurality of gathers of synthetic ultrasound-waveform inversion data, and $\Delta t_i$ represents the time delay corresponding to the i-th single-point gather, and $p_j$ represents a ray parameter of a j-th plane-wave or fan-beam data gather with 1≤j≤s', where the computed synthetic ultrasound-waveform inversion corresponds to the iteration of the synthetic ultrasound-waveform inversion that minimizes $\chi(m)$.

4. The system of claim 3, wherein the function $\chi(m)$ further comprises a regularization term $\mathcal{R}(m)$ added to the plane-wave or fan-beam misfit function, and
wherein the regularization term is:

$$\mathcal{R}(m) = \operatorname{argmin}_m + \lambda_1 \|\nabla m - w\|_l^l + \lambda_2 \|\varepsilon(w)\|_l^l$$

where w is an auxiliary variable, the norm l=½, $\nabla$ is the gradient operator and $\varepsilon$ is the symmetric gradient operator in the second-order form.

5. The system of claim 3, wherein the memory further stores instructions that, when executed by the processor of the host controller, cause the host controller to compute the ultrasound waveform inversion by iteratively minimizing a plane-wave or fan-beam misfit function using an alternating direction minimization strategy and a split-Bregman iteration technique.

6. The system of claim 3, wherein the memory further stores instructions that, when executed by the processor of the host controller, cause the host controller to compute the ultrasound waveform inversion by iteratively minimizing a plane-wave or fan-beam misfit function $\chi$ using an adjoint-state method to compute a gradient for the plane-wave or fan-beam misfit function, and
wherein the gradient is computed by a zero-lag time cross-correlation between a source forward-propagated wavefield and a back-propagated adjoint-source wavefield:

$$\nabla \chi = -\sum_{t,s',r} \frac{\partial^2 p}{\partial t^2} p^\dagger$$

where p is the source wavefield and $p^\dagger$ is the adjoint-source wavefield.

7. The system of claim 3, wherein a nonlinear conjugate-gradient inversion framework is used to update the physical property model m after computing a gradient in each iteration, where a k-th model $m^k$ is updated to compute a k+1-th model $m^{k+1}$ in accordance with:

$$m^{k+1} \leftarrow m^k + \alpha g^k$$

where $\alpha$ is a step length computed using a model perturbation approach, and $g^k$ is the search direction in the k-th iteration computed for a $g^{k+1}$ search direction for a k+1-th iteration using the Polak-Ribière formula:

$$g^{k+1} \leftarrow -(\nabla \chi)^{k+1} + \max\left\{ \frac{[(\nabla \chi)^{k+1}]^T [(\nabla \chi)^{k+1} - (\nabla \chi)^k]}{[(\nabla \chi)^k]^T (\nabla \chi)^k} \right\} g^k,$$

where $(\nabla \chi)^k$ is the gradient in the k-th iteration, and where T represents a transpose operation.

8. The system of claim 1, wherein the memory further stores instructions that, when executed by the processor of the host controller, cause the host controller to:
control the linear ultrasound transducer array to emit plane-wave or fan-beam ultrasound into the biological tissue at a plurality of different angles;
receive plane-wave or fan-beam ultrasound data comprising reflections of the plane-wave or fan-beam ultrasound at each of the plurality of different angles; and
compute a plurality of separate synthetic ultrasound-waveform inversions, each corresponding to the plane-wave or fan-beam ultrasound data received from plane-wave or fan-beam ultrasound emitted at one of the different angles, and
wherein the image of the biological tissue is computed from the separate synthetic ultrasound-waveform inversions of each of the different angles.

9. A method for plane-wave or fan-beam ultrasound tomography comprising:
controlling, by a processor, a multi-channel ultrasound array controller to control a linear ultrasound transducer array to emit plane-wave or fan-beam ultrasound into a biological tissue, the linear ultrasound transducer array comprising a plurality of transducers;
receiving, by the processor, plane-wave or fan-beam ultrasound waveform data from the transducers, the plane-wave or fan-beam ultrasound waveform data comprising reflections of the plane-wave or fan-beam ultrasound from the biological tissue;
computing, by the processor, a synthetic ultrasound-waveform inversion from the received plane-wave or fan-beam ultrasound waveform data; and
computing, by the processor, an image of the biological tissue from the synthetic ultrasound-waveform inversion,
the method further comprising computing the ultrasound waveform inversion by iteratively minimizing a plane-wave or fan-beam misfit function:

$$\chi(m) = \sum_{t,s,r} \frac{1}{2} \|d - f(m)\|_2^2,$$

where d is the plane-wave or fan-beam ultrasound waveform data and f(m) is an iteration of a synthetic ultrasound-waveform inversion, m is a physical parameter model, and a data misfit is accumulated for all recording time (t) of the waveform, all the transducers (s) and all the receivers (r), and where the computed synthetic ultrasound-waveform inversion corresponds to the iteration of the synthetic ultrasound-waveform inversion that minimizes $\chi(m)$.

10. The method of claim 9, wherein the physical parameter model m comprises sound speed values, density values, and attenuation values.

11. A method for plane-wave or fan-beam ultrasound tomography comprising:
controlling, by a processor, a multi-channel ultrasound array controller to control a linear ultrasound transducer array to emit plane-wave or fan-beam ultrasound into a biological tissue, the linear ultrasound transducer array comprising a plurality of transducers;
receiving, by the processor, plane-wave or fan-beam ultrasound waveform data from the transducers, the plane-wave or fan-beam ultrasound waveform data comprising reflections of the plane-wave or fan-beam ultrasound from the biological tissue;
computing, by the processor, a synthetic ultrasound-waveform inversion from the received plane-wave or fan-beam ultrasound waveform data; and
computing, by the processor, an image of the biological tissue from the synthetic ultrasound-waveform inversion,
the method further comprising computing the ultrasound waveform inversion by iteratively minimizing a plane-wave or fan-beam misfit function:

$$\chi(m) = \sum_{t,s',r} \frac{1}{2} \left\| \sum_i^{s'} d_i(\Delta t_i, p_j) - \sum_i^{s'} f_i(m, \Delta t_i, p_j) \right\|_2^2$$

where s' is the number of plane-wave or fan-beam gathers, $d_i$ and $f_i$ are an i-th single-point received ultrasound waveform data and an i-th synthetic ultrasound-waveform inversion data gather of, respectively, a plurality of gathers of received ultrasound data and a plurality of gathers of synthetic ultrasound-waveform inversion data, and $\Delta t_i$ represents the time delay corresponding to the i-th single-point gather, and $p_j$ represents a ray parameter of a j-th plane-wave or fan-beam data gather with $1 \leq j \leq s'$, where the computed synthetic ultrasound-waveform inversion corresponds to the iteration of the synthetic ultrasound-waveform inversion that minimizes $\chi(m)$.

12. The method of claim 11, wherein the function $\chi(m)$ further comprises a regularization term $\mathcal{R}(m)$ added to the plane-wave or fan-beam misfit function, and
wherein the regularization term is:

$$\mathcal{R}(m) = \mathrm{argmin}_m + \lambda_1 \|\nabla m - w\|_l^l + \lambda_2 \|\varepsilon(w)\|_l^l$$

where w is an auxiliary variable, the norm $l=\frac{1}{2}$, $\nabla$ is the gradient operator and $\varepsilon$ is the symmetric gradient operator in the second-order form.

13. The method of claim 12, further comprising computing the ultrasound waveform inversion by iteratively minimizing a plane-wave or fan-beam misfit function using an alternating direction minimization strategy and a split-Bregman iteration technique.

14. The method of claim 11, further comprising computing the ultrasound waveform inversion by iteratively minimizing a plane-wave or fan-beam misfit function $\chi$ using an adjoint-state method to compute a gradient for the plane-wave or fan-beam misfit function, and
wherein the gradient is computed by a zero-lag time cross-correlation between a source forward-propagated wavefield and a back-propagated adjoint-source wavefield:

$$\nabla \chi = - \sum_{t,s',r} \frac{\partial^2 p}{\partial t^2} p^\dagger$$

where p is the source wavefield and $p^\dagger$ is the adjoint-source wavefield.

15. The method of claim 11, wherein a nonlinear conjugate-gradient inversion framework is used to update the physical property model m after computing a gradient in each iteration, where a k-th model $m^k$ is updated to compute a k+1-th model $m^{k+1}$ in accordance with:

$$m^{k+1} \leftarrow m^k + \alpha g^k$$

where $\alpha$ is a step length computed using a model perturbation approach, and $g^k$ is the search direction in the k-th iteration computed for a $g^{k+1}$ search direction for a k+1-th iteration using the Polak-Ribière formula:

$$g^{k+1} \leftarrow -(\nabla \chi)^{k+1} + \max\left\{ \frac{[(\nabla \chi)^{k+1}]^T [(\nabla \chi)^{k+1} - (\nabla \chi)^k]}{[(\nabla \chi)^k]^T (\nabla \chi)^k} \right\} g^k,$$

where $(\nabla \chi)^k$ is the gradient in the k-th iteration, and where T represents a transpose operation.

16. The method of claim 9, further comprising:
controlling the linear ultrasound transducer array to emit plane-wave or fan-beam ultrasound into the biological tissue at a plurality of different angles;
receiving plane-wave or fan-beam ultrasound data comprising reflections of the plane-wave or fan-beam ultrasound at each of the plurality of different angles; and
computing a plurality of separate synthetic ultrasound-waveform inversions, each corresponding to the plane-wave or fan-beam ultrasound data received from plane-wave or fan-beam ultrasound emitted at one of the different angles,
wherein the image of the biological tissue is computed from the separate synthetic ultrasound-waveform inversions of each of the different angles.

* * * * *

UNITED STATES PATENT AND TRADEMARK OFFICE
CERTIFICATE OF CORRECTION

PATENT NO. : 11,284,858 B1
APPLICATION NO. : 16/460899
DATED : March 29, 2022
INVENTOR(S) : Lianjie Huang et al.

It is certified that error appears in the above-identified patent and that said Letters Patent is hereby corrected as shown below:

In the Claims

Column 17, Line 28, Claim 4:
Delete "$\mathcal{R}(m)=\mathrm{argmin}_m+\lambda_1\|\nabla m-w\|_l^l+\lambda_2\|\varepsilon(w)\|_l^l$"
Insert -- $\mathcal{R}(m) = \mathrm{argmin}_m \lambda_1 \|\nabla m - w\|_l^l + \lambda_2 \|\mathcal{E}(w)\|_l^l$ --

Column 19, Line 45, Claim 12:
Delete "$\mathcal{R}(m)=\mathrm{argmin}_m+\lambda_1\|\nabla m-w\|_l^l+\lambda_2\|\epsilon(w)\|_l^l$"
Insert -- $\mathcal{R}(m) = \mathrm{argmin}_m \lambda_1 \|\nabla m - w\|_l^l + \lambda_2 \|\mathcal{E}(w)\|_l^l$ --

Signed and Sealed this
Ninth Day of May, 2023

*Katherine Kelly Vidal*
Katherine Kelly Vidal
*Director of the United States Patent and Trademark Office*